US012053511B2

(12) United States Patent
Eaves-Pyles et al.

(10) Patent No.: US 12,053,511 B2
(45) Date of Patent: Aug. 6, 2024

(54) CYSTATIN C AND Cystatin 9 TO TREAT GUT INFLAMMATION CAUSED BY THERMAL INJURY

(71) Applicant: BOARD OR REGENTS, THE UNIVERSITY OF TEXAS SYSTEM, Austin, TX (US)

(72) Inventors: Tonyia Eaves-Pyles, Galveston, TX (US); Richard B. Pyles, Galveston, TX (US)

(73) Assignee: BOARD OR REGENTS, THE UNIVERSITY OF TEXAS SYSTEM, Austin, TX (US)

(*) Notice: Subject to any disclaimer, the term of this patent is extended or adjusted under 35 U.S.C. 154(b) by 253 days.

(21) Appl. No.: 16/903,107

(22) Filed: Jun. 16, 2020

(65) Prior Publication Data

US 2020/0306351 A1 Oct. 1, 2020

Related U.S. Application Data

(63) Continuation-in-part of application No. 15/826,150, filed on Nov. 29, 2017, now abandoned.

(60) Provisional application No. 62/428,421, filed on Nov. 30, 2016.

(51) Int. Cl.
| | |
|---|---|
| *A61K 38/00* | (2006.01) |
| *A61K 38/57* | (2006.01) |
| *A61K 47/60* | (2017.01) |
| *A61P 1/00* | (2006.01) |
| *A61P 29/00* | (2006.01) |
| *A61P 31/04* | (2006.01) |
| *A61P 37/02* | (2006.01) |
| *C07K 14/81* | (2006.01) |

(52) U.S. Cl.
CPC .............. *A61K 38/57* (2013.01); *A61K 47/60* (2017.08); *A61P 1/00* (2018.01); *A61P 29/00* (2018.01); *A61P 31/04* (2018.01); *A61P 37/02* (2018.01); *C07K 14/8139* (2013.01)

(58) Field of Classification Search
None
See application file for complete search history.

(56) References Cited

U.S. PATENT DOCUMENTS

| | | | |
|---|---|---|---|
| 7,022,734 B2 | 4/2006 | Kazmierski et al. | |
| 9,227,997 B2 | 1/2016 | Park et al. | |
| 9,351,983 B2 | 5/2016 | Corda et al. | |

OTHER PUBLICATIONS

Sun et al., Intensive Care Res., 7 page (published online May 2022) (Year: 2022).*
Costantini et al., J. Trauma 67:1162-1168 (2009) (Year: 2009).*
Greenhalgh, Burns & Trauma 5:10 pages (2017) (Year: 2017).*
"Modulate", Medical Dictionary, available online at https://medical-dictionary.thefreedictionary.com/modulate#:~:text=1.,bil%E2%80%B2i%C2%B7ty%20n, 2 pages (accessed on Jun. 18, 2022) (Year: 2022).*
Zhang et al., Burns & Trauma 9:16 pages (2021) (Year: 2021).*
Chakraborty et al., Systemic Inflammatory Response Syndrome. [Updated May 29, 2023]. In: StatPearls [Internet]. Treasure Island (FL): StatPearls Publishing; Jan. 2023—. Available from: www.ncbi.nlm.nih.gov/books/NBK547669/ (Year: 2023).*
Waxman, www.todaysverterinarynurse.com, p. 35-43 (2020) (Year: 2020).*
Boisset, S et al., "New Therapeutic Approaches for Treatment of Tularaemia": a Review:, Cellular and Infection Microbiology, 2014.
Borman, "New Rules for Gram-negative antibiotics", Chem.Eng. vol. 95, Issue 20, News 95:12 (2017) (Year: 2017).
Burdette, "Systemic Inflammatory Response Syndrome (SIRS)", available online at http://www.antimicrobe.org/e20.asp, 4 pages (first available 2010) (Year: 2010).
Degim etal., "Controlled Delivery of Peptides and Proteins" , Curr. Pharm. Des. 13:99-117, (2007).
Dictionary-Synergy "Synergy" Dictionary.com, available online at https://www.dictionary.com/browse/synergy, 6 pages (accessed on Apr. 28, 2019) (Year: 2019).
Falagas et al., "Polymyxins," available online at http://www.antimicrobe.org/d05.asp, 20 pages (first available 2010) (Year: 2010).
Hoerr et al., "Gram-Negative and Gram-Positive Bacterial Infections Give Rise t a Different Metabolic Response in a Mouse Model", Journal of Proteome Research, 11 :3231-3245 (2012) (Year: 2012).
Kaplan, "Systemic Inflammatory Response Syndrome" available online at https://emedicine.medscape.com/article/168943-clinical, 22 pages (2018) (Year: 2018).
Leon-Sicairos, "Strategies of Intracellular Pathogens for Obtaining Iron from the Environment", Bio Med Res. Intl. 2015:1-17 (2015) (Year: 2015).
Mendes et al., "Polymyxins—A Review Focusing on Their Nephrotoxicity", Rev. Assoc. Med. Bras. 56:752-758 (2010) (Year: 2010).
"Prevent", Merriam Webster Dictionary, available online at https://www.merriam-webster.com/dictionary/prevent, 12 pages (accessed on Apr. 29, 2019) (Year: 2019).
"Restrain", Merriam Webster Dictionary, available online at https://www.merriam-webster.com/dictionary/restrain, 12 pages (accessed on Apr. 29, 2019) (Year: 2019).
NCI-Dictionary of Cancer Terms, "Concomitant", National w Cancer Institute, available online at https://www.cancer.gov/publications/dictionaries/cancer-terms/def/concomitant, 1 page (accessed on Apr. 28, 2019) (Year: 2019).

(Continued)

*Primary Examiner* — Thea D'Ambrosio
(74) *Attorney, Agent, or Firm* — Edwin S. Flores; Daniel J. Chalker; Chalker Flores, LLP

(57) ABSTRACT

The present invention includes a composition and method of modulating a dysregulated gut-derived inflammation following a thermal injury comprising: identifying a mammal in need of treatment for the dysregulated gut-derived inflammation following the thermal injury; and providing the mammal with a recombinant Cystatin 9 (CST9) and Cystatin C (CSTC) in a synergistic amount sufficient to restrain or prevent a life-threatening, unrestrained systemic dysregulated gut-derived inflammation in the mammal caused by the thermal injury.

6 Claims, 19 Drawing Sheets

(56) References Cited

OTHER PUBLICATIONS

Veronese et al., "The Impact of PEGylation on Biological Therapies" Biodrugs 22:315-329 (2008) (Year: 2008).
Barantsevich, E.P., et al. "Emergence of Klebsiella pneumoniae producing NDM-1 carbapenemase in Saint Petersburg, Russia," J Antimicrob Chemother (2013), 68:1204-6.
Bauer, T.T., et al. "Acute respiratory distress syndrome and pneumonia: a comprehensive reivew of clinical data." Clin Infect Dis (2006), 43:748-756.
Björck, L., et al. "Cystatin C, a human proteinase inhibitor, blocks replication of herpes simplex virus." J Virol (1990), 64:941-3.
Bobek, L.A., et al. "Cystatins-inhibitors of cysteine proteinases." Crit Rev Oral Biol Med (1992), 3:307-332.
Bosch, T., et al. "An Outbreak of NDM-1-Producing Klebsiella pneumoniae in a Dutch Hospital, with Interspecies Transfer of the Resistance Plasmid and Unexpected Occurrence in Unrelated Health Care Centers." J Clin Microbiol (2017), 55:2380-2390.
Cimerman, N., et al. "Characterization of cystatin C from bovine parotid glands: cysteine proteinase inhibition and antiviral properties." Biol Chem Hoppe Seyler (1996), 377:19-23.
Coban, A.Y., "Rapid determination of methicillin resistance among *Staphyloccus aureus* clinical isolates by colorimetric methods." J Clin Micro (2012), 50:2191-2193.
Docobo-Pérez, F., et al. "Efficacies of colistin and tigecycline in mice with experimental pneumonia due to NDM-1-producing strains of Klebsiella pneumoniae and *Escherichia coli*." Int J Antimicrob Agents (2011), 39:251-4.
Eaves-Pyles, T.D., et al. "*Salmonella flagellin*-dependent proinflammatory responses are localized to the conserved amino and carboxyl regions of the protein." J Immunol (2001), 167:7009-16.
Eaves-Pyles, T., et al. Immunomodulatory and antibacterial effects of cystatin 9 against Francisella tularensis. Mol Med (2013), 19:263-275.
Ervin, H., et al. "Late stage inhibition of hematogenous melanoma metastasis by cystatin C over-expression." Cancer Cell Int (2005), 5:14.
Falagas, M.E., et al. "Colistin: the revival of polymyxins for the management of multidrug-resistant gram-negative bacterial infections." Clin Infect Dis (2005), 40:1333-41.
Gauthier, S., et al. "Protective mechanisms by cystatin C in neurodegenerative diseases." Front Biosci (Schol Ed) (2011), 3:541-554.
Gurjar, M. "Colistin for lung infection: an update." J Intensive Care (2015), 3:3.
Halaby, T., et al. "A Case of New Delhi Metallo-β-Lactamase 1 (NDM-1)-Producing Klebsiella pneumoniae with Putative Secondary Transmission from the Balkan Region in the Netherlands." Antimicrob Agents Chemother (2012), 56:2790-2791.
Harris, J.M., et al. "Effect of pegylation on pharmaceuticals." Nat Rev Drug Discov (2003), 2:214-21.
Hickman-Davis, J.M., et al. "Killing of Klebsiella pneumonia by human alveolar macrophages." Am J Physiol Lung Cell Mol Physiol (2002), 282: L944-L956.33.
Hudson, C.M., et al. "Resistance Determinants and Mobile Genetic Elements of an NDM-1-Encoding Klebsiella pneumoniae Strain." PLoS One (2014), 9:e99209.
Kaeser, S., et al. "Cystatin C modulates cerebral β-amyloidosis." Nat Genet (2007), 39:1437-1439.
Kar, S., et al. "Cystatin cures visceral leishmaniasis by $NF_{-\kappa}B$-mediated proinflammatory response through co-ordination of TLR/MyD88 signaling with p105-Tpl2-ERK pathway." Eur J Immunol (2011), 41:116-27.

Kaur, G., et al. "Cystatin C in Alzheimer's disease." Front Mol Neurosci (2012), 5:79.
Khalil, M.A.F., et al. "Emergence of Multidrug-Resistant New Delhi Metallo-β-Lactamase-1-Producing Klebsiella pneumoniae in Egypt." Microb Drug Resist (2017), 23:480-487.
Khan, A.U., et al. "Structure, Genetics and Worldwide Spread of New Delhi Metallo-β-lactamase (NDM): a threat to public health." BMC Microbiol (2017), 17:101.
Kopitar-Jerala, N., "The role of cystatins in cells of the immune system." FEBS Lett (2006), 580:6295-6301.
Lee, C.-R., et al. "Global Dissemination of Carbapenemase-Producing Klebsiella pneumoniae: Epidemiology, Genetic Context, Treatment Options, and Detection Methods." Front Microbiol (2016), 7:895.
Li, J.J., et al. "New Delhi Metallo-β-Lactamase-1-Producing Klebsiella pneumoniae, Florida, USA." Emerg Infect Dis (2016), 22:744-6.
Liang, Z., et al. "Molecular Basis of NDM-1, a New Antibiotic Resistance Determinant." PLOS One (2011), 6: e23606.
Loffek, S., et al. "Series Matrix metalloproteinases in lung health and disease: Biological role of matrix metalloproteinases: a critical balance." Eur Respir J (2011), 38:191-208.
Magister, Š., et al. Cystatins in Immune System. J Cancer (2013), 4:45-56.
Mattheolabakis, G., et al. "Pegylation improves the pharmacokinetics and bioavailability of small-molecule drugs hydrolyzable by esterases: a study of phospho-Ibuprofen." J Pharmacol Exp Ther (2014), 351:61-635.
Ochieng, J., et al. "Cystatin superfamily." J Health Care Poor Underserved (2010), 21:51-70.
Okamoto, T., et al. "Molecular mechanism for activation and regulation of matrix metalloproteinases during bacterial infections and respiratory inflammation." Biol Chem (2004), 385:997-1006.
Pesesky, M.W., et al. "KPC and NDM-1 Genes in Related Enterobacteriaceae Strains and Plasmids from Pakistan and the United States." J Emerg Infect Dis (2015), 21:1034-1037.
Pitout, J.D., et al. "Carbapenemase-Producing Klebsiella pneumoniae, a Key Pathogen Set for Global Nosocomial Dominance." Antimicrob Agents Chemother (2015), 59:5873-84.
Poteryaeva, O.N., et al. "Cysteine proteinase inhibitor level in tumor and normal tissues in control and cured mice." Drugs Exp Clin Res (2000), 26:301-306.
Pyles, R.B., et al. "Toll-Like Receptor 3 Agonist Protection against Experimental Francisella tularensis Respiratory Tract Infection." Infect Immun (2010), 78:1700-1710.
Rivera, L.E., et al. "Macrophage derived cystatin B/cathepsin B in HIV replication and neuropathogenesis." Curr HIV Res (2014), 12:111-120.
Robilotti, E., et al. "Carbapenemase-producing Klebsiella pneumoniae." F1000Prime Rep (2014), 6: 80.
Tian, M., et al. "Preclinical Efficacy of Cystatin C to Target the Oncogenic Activity of Transforming Growth Factor β in Breast Cancer." Transl Oncol (2009), 2:174-183.
Vray B., et al. "Immunomodulatory properties of cystatins." Cell Mol Life Sci (2002), 59:1503-1512.
Zavasnik-Bergant T. "Cystatin protease inhibitors and immune functions." Front Biosci (2008), 13:4625-4637.
Zhu, K., et al. "A quantum mechanics/molecular mechanics study on the hydrolysis mechanism of New Delhi metallo-β-lactamase-1." J Comput Aided Mol Des (2013), 27:247-56.
Zmarlicka, M.T., et al. "Impact of the New Delhi metallo-beta-lactamase on beta-lactam antibiotics." Infect Drug Resist (2015), 8:297-309.

* cited by examiner

FIG. 3

CYSTATIN C AND Cystatin 9 TO TREAT GUT INFLAMMATION CAUSED BY THERMAL INJURY

CROSS-REFERENCE TO RELATED APPLICATIONS

This is a continuation-in-part application of U.S. patent application Ser. No. 15/826,150, filed Nov. 29, 2017, and is a non-provisional Patent Application claims priority to U.S. Provisional Patent Application Ser. No. 62/428,421, filed on Nov. 30, 2016, entitled "Cystatin C and Cystatin 9 to Treat Inflammation Caused by Bacteria" the contents of which is incorporated by reference herein in its entirety.

STATEMENT OF FEDERALLY FUNDED RESEARCH

This invention was made with government support under R21AI06877402 awarded by NIH/NIAID. The government has certain rights in the invention.

TECHNICAL FIELD OF THE INVENTION

The present invention relates in general to the field of inflammation, and more particularly, to treatment of conditions such as sepsis and septic shock.

BACKGROUND OF THE INVENTION

Without limiting the scope of the invention, its background is described in connection with systemic inflammatory conditions.

Systemic inflammatory conditions are one class of diseases for which early diagnosis is particularly desirable, with sepsis being the most serious. Sepsis is the result of the interaction of a pathogenic microorganism with a host's immune system that leads to systemic inflammation. The characterization of sepsis in a host is very complex due to a heterogeneity of factors that play into the final outcome. A number of factors are drivers of the underlying immune response and systemic inflammatory disease, such as, a patient's genetically determined response to immune stimuli, the general status of their immune system, and microbial mediators and virulence factors released by infectious organisms. The progression of a systemic inflammatory diseases is often remarkably rapid, leaving the clinician with little time to make a considered clinical judgment.

U.S. Pat. No. 9,351,983, issued to Corda, et al., entitled, "Use of glycerophosphoinositols for the treatment of septic shock" teaches the use of glycerophosphoinositols (GPIs) and derivatives thereof for use in the treatment of pathologies related to a Lipopolysaccharide (LPS)-activated tissue-factor (TF) activity, as pathologies induced by high bacteremia, i.e. septic shock.

U.S. Pat. No. 9,227,997, issued to Park, et al., entitled, "Composition for treating sepsis or septic shock comprising the peptide originated from the Smad6" teaches a pharmaceutical composition comprising a Smad6-derived peptide as an active ingredient. This composition is said to have the ability to specifically bind to Pellino-1, the Smad6-derived peptide is effectively useful in the treatment of the sepsis mediated by excessively activated TLR, and effectively reduce the expression of inflammatory cytokines, protects cells from sepsis-induced apoptosis, and exhibits high bacterial clearance in animal models of sepsis.

U.S. Pat. No. 7,022,734, issued to Kazmierski, et al., entitled, "Treatment of septic shock" teaches the use of transition metal complexes in the treatment of septic shock, in particular, the hypotension associated therewith and pharmaceutical formulations comprising such complexes are disclosed. The use of such transition metal complexes in the treatment of other conditions caused by pathological NO production are also said to be disclosed.

SUMMARY OF THE INVENTION

In one embodiment, the present invention includes a method of modulating a dysregulated gut-derived inflammation following a thermal injury comprising: identifying a mammal in need of treatment for the dysregulated gut-derived inflammation following the thermal injury; and providing the mammal with a recombinant Cystatin 9 (CST9) and Cystatin C (CSTC) in a synergistic amount sufficient to restrain or prevent a life-threatening, unrestrained systemic dysregulated gut-derived inflammation in the mammal caused by the thermal injury. In one aspect, the rCST9/rCSTC reduces systemic MCP-1, MCP-3, IP-10, IL-6, and GRO-alpha/KC at 24 h post-infection and thermal injury. In another aspect, the CST9 and CSTC maintains at least one of the gut microbiome or maintains an intestinal barrier. In another aspect, the CST9 and CSTC are provided 1, 2, 3, 4, 5, 6, or 7 days post thermal injury. In another aspect, the Cystatin 9 (CST9) and Cystatin C (CSTC) prevent an increase in a Gram-negative *Bacteroidales* population in the gut microbiome. In another aspect, the Cystatin 9 (CST9) and Cystatin C (CSTC) prevent a decrease in Gram-positive *Lachnospiracease* in the gut microbiome. In another aspect, the composition is adapted for intraperitoneal, intravenous, parenteral, enteral, pulmonary, intranasal, intramuscular, rectal, or oral administration. In another aspect, at least one of the Cystatin 9 (CST9) or Cystatin C (CSTC) are provided in an amount of 1-500 picograms/kilo. In another aspect, at least one of the Cystatin 9 (CST9) or Cystatin C (CSTC) is PEGylated. In another aspect, the mammal is a human.

In another embodiment, the present invention includes a method of treating a dysregulated gut-derived inflammation caused by a thermal injury comprising: identifying a mammal in need of treatment for at least one of: a disrupted gut microbiota, damage to an intestinal barrier or intestinal and systemic inflammation following the thermal injury; and providing the mammal with a recombinant Cystatin 9 (CST9) and Cystatin C (CSTC) in a synergistic amount sufficient to restrain or prevent the disrupted gut microbiota, damage to the intestinal barrier or intestinal and systemic inflammation in the mammal caused by the thermal injury. In one aspect, the present invention includes a rCST9/rCSTC reduces systemic MCP-1, MCP-3, IP-10, IL-6, and GRO-alpha/KC at 24 h post-infection and thermal injury. In another aspect, the CST9 and CSTC prevents leakage of an intestinal barrier. In another aspect, the CST9 and CSTC are provided 1, 2, 3, 4, 5, 6, or 7 days post thermal trauma. In another aspect, the Cystatin 9 (CST9) and Cystatin C (CSTC) prevent an increase in a Gram-negative *Bacteroidales* in the gut microbiome. In another aspect, the Cystatin 9 (CST9) and Cystatin C (CSTC) prevent a decrease in Gram-positive *Lachnospiracease* in the gut microbiome. In another aspect, the composition is provided concurrently with one or more antibiotics that are bacteriocidal or bacteriostatic against a pathogenic gut bacteria. In another aspect, the composition is adapted for intraperitoneal, intravenous, parenteral, enteral, pulmonary, intranasal, intramuscular, rectal, or oral administration. In another aspect, at least one of the Cystatin 9 (CST9) or Cystatin C (CSTC) are provided in an amount of 1-500 picograms/kilo. In another aspect, at least one of the Cystatin 9 (CST9) or Cystatin C (CSTC) is PEGylated.

BRIEF DESCRIPTION OF THE DRAWINGS

For a more complete understanding of the features and advantages of the present invention, reference is now made to the detailed description of the invention along with the accompanying figures and in which:

FIG. 3 shows the results from pegylation of rCST9, co-administered with rCSTC, did not improve survival outcomes of NDM-1 Kp infected mice. Balb/c mice (n=15 mice/gp) were i.n. infected with an LD90 challenge with NDM-1 Kp and then treated with an i.n. dose of PEG-rCST9/rCSTC (50 pg of each/mouse) on 1 h PI followed by 500 pg of PEG-rCST9/rCSTC/mouse at 3 d PI or mice were administered a single i.p. dose of PEG-rCST9/rCSTC (500 pg of each/mouse) at 3 d PI. PEG-rCST9/rCSTC did not improve the survival of infected mice that surpassed rCST9/rCSTC. However, both groups that receive the i.p. administration of rCST9 or PEG-rCST9 in combination with rCSTC on day 3 PI significantly increased survival compared to NDM-1 Kp infected mice ($p<0.05$). Data are presented as mean±SEM, and asterisk signifies significant differences of $p<0.05$.

FIG. 4 shows that rCST9/rCSC treatment improves survival alone or in combination with a suboptimal low dose of colistin in mice infected with a lethal pulmonary challenge with NDM-1 Kp. Balb/c mice (n=15 mice/gp) were i.n. infected with NDM-1 Kp ($1.82\times10^8$ CFU/mouse) and then given an i.p. dose of 500 pg of both rCST9/rCSTC/mouse at 3 d PI. Then mice were given colistin at 20 or 1.25 mg/kg/mouse i.p. 2 times/day for 2 days at 4 and 5 d PI. rCST treatment worked synergistically with a very low dose of colistin (1.25 mg/kg) to significantly improve and show synergistic survival compared to infected mice ($p<0.05$), and 1.25 mg/kg of colistin alone. Therefore, rCSTs significantly extended the period of survival before suboptimal low dose of antibiotic treatment was needed/initiated. Data are presented as mean±SEM, and asterisk signifies significant differences of $p<0.05$.

FIG. 5A shows that rCST9/rCSTC treatment modulated inflammatory responses and preserved lung integrity in a mouse model of pneumonia. Balb/c mice (n=6 mice/gp) were i.n. infected with NDM-1 Kp ($1.82\times10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Serum was collected and lungs, livers, and spleens were harvested at 5 days PI. Fold change in the overall cytokine levels in the serum (FIG. 5A) of rCST treated mice were decreased compared to untreated in NDM-1 infected mice.

FIG. 5B shows that rCST9/rCSTC treatment modulated inflammatory responses and preserved lung integrity in a mouse model of pneumonia. Balb/c mice (n=6 mice/gp) were i.n. infected with NDM-1 Kp ($1.82\times10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Serum was collected and lungs, livers, and spleens were harvested at 5 days PI. Fold change in the overall cytokine levels in the lungs (FIG. 5B) of rCST treated mice were decreased compared to untreated in NDM-1 infected mice.

FIG. 5C shows that rCST9/rCSTC treatment modulated inflammatory responses and preserved lung integrity in a mouse model of pneumonia. Balb/c mice (n=6 mice/gp) were i.n. infected with NDM-1 Kp ($1.82\times10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Both rCST9/rCSTC treatments modulated cytokine secretion in the serum (FIG. 5C).

FIG. 5D shows that rCST9/rCSTC treatment modulated inflammatory responses and preserved lung integrity in a mouse model of pneumonia. Balb/c mice (n=6 mice/gp) were i.n. infected with NDM-1 Kp ($1.82\times10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Both rCST9/rCSTC treatments modulated cytokine secretion in all tested organs (FIG. 5D).

FIGS. 5E to 5H shows that rCST9/rCSTC treatment modulated inflammatory responses and preserved lung integrity in a mouse model of pneumonia. Balb/c mice (n=6 mice/gp) were i.n. infected with NDM-1 Kp ($1.82\times10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Both rCST9/rCSTC treatments significantly reduced bacterial burden in the lungs (E). Lung histology (H&E; 40× mag) from the same treated and/or infected mice showed that both rCST treatment regimens minimalized lung pathology caused by NDM-1 Kp (FIG. 5F). rCST treatment reduced apoptotic cells compared to untreated/infected mice (FIG. 5G). MDA detection in the lungs was significantly decreased in rCST-treated and infected mice (FIG. 5H). Data are presented as mean±SEM, and asterisk signifies significant differences of $p<0.05$.

FIGS. 6A to 6C show that rCST treatments preserved lung integrity and prevented long-term lung damage. Balb/c mice (n=4 mice/gp) were i.n. infected with NDM-1 Kp ($1.82\times10^8$ CFU/mouse) and then treated with an i.n. dose of rCST9/rCSTC (50 pg of each). The lungs were harvested at 24 h and 72 h PI. A parallel group of mice were infected and treated i.n./i.p. or i.p with rCST9/rCSTC as described herein, and then lungs were harvested on 5 and 10 d PI. Serial sections of the lung were analyzed for histology (40× mag) and apoptosis by using the TUNEL assay with DAPI to stain cell nuclei. FIG. 6A shows the i.n. administration of rCST9/ rCSTC to infected mice markedly diminished immune cell infiltration into the lungs and edema at 24 h and 72 h PI compared to high cellularity and signs of hemorrhaging and edema in the lungs of untreated, infected mice. Further, lungs from our two optimal rCST9/rCSTC treatments on 5 d and 10 d PI prevented long-term lung damage and showed resolution of inflammation.

DETAILED DESCRIPTION OF THE INVENTION

Figure 1:
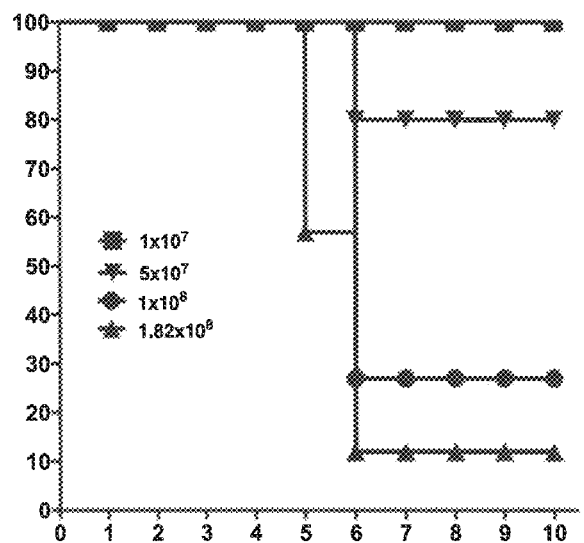
FIG. 1 shows the establishment of LD90 NDM-1 Kp pneumonia murine model. Balb/c mice (n=20 mice/group) were intranasally (i.n.) inoculated with various challenge doses of NDM-1 Kp and their survival was observed for 10 d. The LD90 of Kp resulted in $1.82 \times 10^8$ CFU per mouse.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Abbreviations. rCST9: recombinant cystatin 9, rCSTC: recombinant cystatin C, rCST9/rCSTC or rCSTs: recombinant cystatin 9 and cystatin C, IECs: intestinal epithelial cells, EC: *E. coli* 083:H1, TBSA: full-thickness thermal injury, LPS: lipopolysaccharides, multidrug-resistant: MDR, New Delhi metallo-beta-lactamase (NDM-1), Flag: flagellin, TLR5: toll-like receptor 5, HEK: human embryonic kidney, min: minute, GRO-alpha/KC/CINC1: growth-related oncogene alpha/equivalent to human interleukin-8/cytokine-induced neutrophil chemoattractant, MCP-1: monocyte chemoattractant protein-1, MCP-3: monocyte chemoattractant protein-3, IP-10: Interferon gamma-induced protein, IL-6: interleukin-6.

Cystatins are inhibitors of the lysosomal cysteine proteinases, cathepsin B, L, H and S and can function extracellularly and intracellularly. These inhibitors have been shown to regulate and give protection to the host against uncontrolled proteolysis in various disease processes namely cancer and neurodegeneration. As such cystatins have been shown to modulate inflammation, prevent the metastasis of tumor cells and protect healthy tissue against penetration of bacteria. Therefore, cystatins have been studied as a potential therapeutic agent for certain cancers and a biomarker for antitumor therapy. Additionally, cystatin was upregulated in LP-stimulated cancer cells suggesting that the inhibition of the secreted form of cysteine proteinases prevents inflammatory tissue injury. Cystatin 9 (CST9) and cystatin C (CSTC) are a small 18 kDa protein that can be secreted and found in human fluids as well as expressed in the lungs, liver, heart, pancreas, skeletal muscle and placenta. Although little is known about CST9, it is thought to play a role in inflammation but it's role is unknown specifically during pathogenic bacterial infections. CSTC has been well studied as a potential therapeutic agent to prevent and/or restrain neurodegeneration and metastasis of tumor cells. Cystatin 9 (Homo sapiens cystatin 9 (testatin) (CST9) has NCBI Reference Sequence: NM 001008693.2, Gene ID: 128822, relevant sequences incorporated herein by reference. Cystatin C (CSTC) or Homo sapiens cystatin C (CST3), transcript variant 2, mRNA, has NCBI Reference Sequence: NM_001288614.1, Gene ID: 1471, relevant sequences incorporated herein by reference.

As used herein, the term "pharmaceutically effective amount" refers to that amount of an agent effective to produce the intended effect of reducing, preventing and/or modulating immune responses and thereby inducing controlled, beneficial inflammation against bacterial pathogens, such as Gram negative bacteria or multiple drug resistant bacteria. Generally, the compositions and method of the present invention prevent or reduce run-away immune responses caused by an over-reaction by the immune response to the pathogen, leading to severe immune-mediated shock, e.g., septic shock, acute lung injury (ALI), acute respiratory distress syndrome (ARDS), and systemic inflammation. Such factors include the generation of a cytokine cascade, hypercytokemia, or cytokine storm that is a potentially fatal immune reaction. For example, the cytokine storm generally includes a positive feedback loop between cytokines and white blood cells leading to highly elevated levels of various cytokines. It has been found that the present invention helps to ameliorate or lessen the release of both pro-inflammatory cytokines (e.g., Tumor Necrosis Factor-alpha, Interleukin-1, and Interleukin-6) and anti-inflammatory cytokines (e.g., Interleukin-10 and Interleukin-1 receptor antagonist), which are commonly elevated in the serum of patients experiencing a cytokine storm. Specifically, but not a limitation of the present invention, the present inventors have studied the effect of the compositions and methods of the present invention looking at, at least, GRO-alpha/KC/CINC1, IL-1Beta, MIP-1alpha, TNF-alpha, IL-6, IP-10 and IL-23.

As used herein, the term "cytokine storm" refers to the dysregulation of cytokines leading to disease that is also referred to as "cytokine release syndrome" or "inflammatory cascade". Often, a cytokine storm or cascade is referred to as being part of a sequence because one cytokine typically leads to the production of multiple other cytokines that can reinforce and amplify the immune response. Generally, these pro-inflammatory mediators have been divided into two subgroups: early mediators and late mediators. Early mediators, such as e.g., Tumor-Necrosis Factor, Interleukin-1, Interleukin-6, are not sufficient therapeutic targets for re-establishing homeostatic balance because they are resolved within the time frame of a patient's travel to a clinic to receive medical attention. In contrast, the so-called "late mediators" have been targeted because it is during this later "inflammatory cascade" that the patient realizes that he or she has fallen ill.

In certain aspects the Cystatin 9 or Cystatin C is postranslationally modified by changes in, e.g., glycosylation, lipidation, PEGylation, and the like, to enhance one or more physiological characteristics during use, such as, e.g., increased resistance to degradation, increased half-life, enhanced activity, etc.

Generally, a cytokine cascade is a healthy systemic expression of the immune system, however, when the cascade enters a positive feedback loop without control it is referred to as a cytokine storm. The present invention can be used to reduce or eliminate some or most of an exaggerated immune response caused by, e.g., rapidly proliferating and highly activated T-cells or natural killer (NK) cells that results in the release of the "cytokine storm" that can include more than 150 inflammatory mediators (cytokines, oxygen free radicals, and coagulation factors). Both pro-inflammatory cytokines (such as Tumor Necrosis Factor-α, Interleukin-1, and Interkeukin-6) and anti-inflammatory cytokines (such as Interleukin-10, and Interleukin-1 receptor antagonist (IL-1RA)) become greatly elevated in, e.g., serum. It is this excessive release of inflammatory mediators that triggers the "cytokine storm."

In the absence of prompt intervention, such as that provided by the present invention, a cytokine storm can result in permanent lung damage and, in many cases, death. The end stage symptoms of the cytokine storm include but are not limited to: hypotension; tachycardia; dyspnea; fever; ischemia or insufficient tissue perfusion; uncontrollable hemorrhage; severe metabolism dysregulation; and multi-system organ failure.

As used herein, the term "treatment" refers to the treatment of the conditions mentioned herein, particularly in a patient who demonstrates symptoms of the disease or disorder. As used herein, the term "treating" refers to any administration of a compound of the present invention and includes (i) inhibiting the disease in an animal that is experiencing or displaying the pathology or symptomatology of the diseased (i.e., arresting further development of the pathology and/or symptomatology) or (ii) ameliorating the disease in an animal that is experiencing or displaying the pathology or symptomatology of the diseased (i.e., reversing the pathology and/or symptomatology). The term "controlling" includes preventing, treating, eradicating, ameliorating or otherwise reducing the severity of the condition being controlled.

As used herein, the terms "effective amount" or "therapeutically effective amount" refer to an amount of a subject compound that will elicit the biological or medical response of a tissue, system, animal or human that is being sought by the researcher, veterinarian, medical doctor or other clinician. In one example, the therapeutically effective amount comprises 1 to 500 picograms/kg, 10 to 100 picograms/kg, 25 to 75 picograms/kg, 10, 20, 30, 40, 50, 60, 70, 80, 90, or 100, 125, 150, 175, 200, 225, 250, 275, 300, 325, 350, 375, 400, 425, 450, 475 and 500 picograms/kg of body weight of the subject.

As used herein, the terms "administration of" or "administering a" when referring to a compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as intravenous (IV), intramuscular (IM), or intraperitoneal (IP), intranasal (IN), intrapulmonary, and the like; enteral or parenteral, transdermal dosage forms, including creams, jellies, powders, or patches; buccal dosage forms; inhalation powders, sprays, suspensions, and the like; and rectal suppositories. For example, the term "intravenous administration" includes injection and other modes of intravenous administration, and likewise for the other routes of administration.

As used herein, the term "pharmaceutically acceptable" describes a carrier, diluent or excipient must be compatible with the other ingredients of the formulation and not deleterious to the recipient thereof.

As used herein, the term "systemic inflammatory response syndrome (SIRS)" refers to a clinical response to a variety of severe clinical insults, as manifested by two or more of the following: heart rate (HR)>90 beats/minute; respiratory rate (RR)>20 breaths/minute; $P_{CO2}$<32 mmHg, or requiring mechanical ventilation; temperature >38° C. or <36° C.; white blood cell count (WBC) either >12×10$^9$/L or <4.0×0$^9$/L or having >10% immature forms (bands), generally, within a 24 hour period. It is recognized that this represents a consensus definition of SIRS, and that the definition may be modified or supplanted by an improved definition in the future. The present definition is used herein to clarify current clinical practice, and does not represent a critical aspect of the invention.

The compositions of the present invention are typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the composition may be formulated to provide, e.g., maximum and/or consistent dosing for the particular form for oral, rectal, topical, intravenous injection or parenteral administration. While the composition may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); Remington: The Science and Practice of Pharmacy, Pharmaceutical Press; 22nd Edition (2012); all of which are incorporated by reference, and the like, relevant portions incorporated herein by reference.

Although certain levels of inflammation are required for protection against infection, unrestrained inflammation can worsen an infection and/or disease. In fact, exacerbated inflammation can be an advantage to invasion by some mucosal pathogens. Current anti-inflammatory agents typically suppress/inhibit immune responses and/or fail to modulate the extent and intensity of the inflammatory cascade, compromising many aspects of acquired immunity development and leading to an imbalance of immune functions and increased risk of exacerbated primary and/or secondary infections. The present invention includes the immunomodulatory functions of the recombinant human protein rCST9 and rCSTC as an innovative and effective approach to modulate immune responses and thereby inducing controlled, beneficial inflammation against Gram-negative pathogens. rCST9 and rCSTC also generated direct antimicrobial outcomes that contributed to significant improvements in survival outcomes in several challenge models.

Example 1

The present inventors show herein that rCST9 and rCSTC restrain and/or prevent life-threatening, unrestrained immune responses in the host against pathogenic bacteria. They further show that rCST9 and rCSTC have protective effects against various bacterial pathogens thus they could be potentially used as a treatment (alone and/or in combination with other treatments such as antibiotics) and/or intervention for multiple infectious agents.

Following cloning and purification of rCST9, the inventors show the protective effects engendered by rCST9 (50 pg dose) whereby this inhibitor retarded the viability and virulence of various pathogenic bacterial strains such as *Burkholderia thialandensis* (ATCC), *Klebsellia pneumoniae* (isolate from burn patient lung), *E. coli* O157:H7 (ATCC), *Pseudomonas aeruginosa* (isolate from burn patient wound), and *Salmonella typhimurium* (ATCC). Further, rCST9 induced human monocyte-derived macrophage (MDM) killing of these same pathogens. Additionally, both rCST9 and rCSTC, given individually and in combination with one another, inhibited the replication of the multi-drug resistant New Delhi metallo-β-lactamase (NDM-1)-producing *Klebsellia pneumonia* (Kp). Likewise, rCSTC (50 pg) and rCST9 (25 or 50 pg), given individually and in combination, restrained cytokine secretion from monocyte-derived macrophages (MDM) infected with New Delhi metallo-β-lactamase (NDM-1)-producing Kp compared to Kp-infected MDM. These in vivo data show that the combination of rCST9 and rCSTC administered at a dose of 50 pg/CST intranasally (i.n.) and/or 500 pg intraperitoneally (i.p.) significantly improved host survival in an experimental model of pneumonia caused by drug-resistant Delhi metallo-beta-lactamase-1 (NDM-1) producing Kp.

It is known that intestinal leakage of intestinal bacteria and their product occurs following burn injury likely contributing to systemic infection and sepsis. The present inventors have shown that individual treatments of rCST9 or rCSTC or the combination of both decreased IL-8 secretion from intestinal epithelial cells following exposure to enteric *E. coli* 083:H1 and/or flagellin. Balb/c mice gavaged with rCST9 or rCSTC (50 pg/mouse) then immediately given a 30% full-thickness burn showed a decrease in systemic MIP-1 and IL-8 secretion, specifically in the lungs, as induced by gut-derived enteric *E. coli* 083:H1 and/or flagellin as compared to controls. Additionally, rCST9 and rCSTC preserved the gut microbiome in these same animals.

The optimized recombinant cystatin 9 (rCST9) or PEG recombinant cystatin C (rCST9) were used to minimize Acute lung injury/acute respiratory distress syndrome (ALI/ARDS) and systemic inflammation resulting in improved survival (e.g. increased survival of 10-25% vs. infection alone) in an experimental mouse model of drug-resistant bacterial and viral pneumonia. The most effective dosage regime for rCST9 against New Delhi metallo-beta-lactamase-1 (NDM-1)-producing *K. pneumoniae* (Kp) pneumonia can be determined.

To establish the optimal CST route, timing, and dosage regimen against MDR NDM-1 Kp-induced pneumonia, Balb/c mice (n=10-20 mice/gp) were infected with an i.n. LD90 and treated at various times and doses as depicted in Table 1. Doses included i.n. and/or i.p. single rCST9, rCSTC or a combination of rCST9 and rCSTC. Mice that were infected with NDM-1 Kp but were not treated served as controls. rCST treatments by routes, doses, or as a combined therapy were studied to select an optimal regimen. The results showed that the i.n. monotherapy treatment with either rCST9 or rCSTC at 50 or 500 pg delivered 1 d and/or 3 d PI increased survival between 5-20% compared to findings with untreated NDM-1 Kp-infected mice. However, specific timing and route of the combination of rCST9/rCSTC PI markedly improved survival of Kp-infected mice compared to those given individual treatments (Table 1). Mice treated i.n. with rCST9/rCSTC (50 pg of each) at 1 h PI and then given rCST9/rCSTC (500 pg of each) i.p. at 3 d PI significantly improved survival outcomes compared to the other groups in the study except one additional dosage regimen (Table 1; p<0.05). Interestingly, nearly equivalent survival was observed when a single i.p. dose of rCST9/rCSTC (500 pg/mouse) was given 3 d PI compared to survival rates in untreated NDM-1 Kp-infected mice (Table 1; <0.05).

Evaluate optimal timing and dosage of rCST-9 and/or PEG-rCST9 administration post-infection. Balb/c mice (n=10-20 mice/gp) were intranasally (i.n.) infected with approximately 1.82×108 CFU/mouse of Kp 2146 (as established hereinabove) then treated i.n. or i.p. with rCST9, human recombinant cystatin C (rCSTC) or a combination of rCST9 and rCSTC as depicted in Table 1. Kp infected alone served as controls. Additionally, another cysteine proteinase inhibitor, CSTC, has been shown to induce anti-apoptotic pathways in neurons and possess anti-microbial activity against Gram-positive pathogens. Therefore, as a comparative control to rCST9, the inventors evaluated the effectiveness of rCSTC against pneumonia using the same doses of 50 and/or 500 pg/mouse. These results show that individually administered rCST9 or rCSTC increased survival 10-15% of Kp-infected mice (LD90) depending on timing (1 h and or/3 d post-infection [PI]), route (i.n. and/or intraperitoneal (i.p.)) and dose (50 pg and/or 500 pg) [Table 1]. Table 1 shows the results from Cystatin treatment regime(s) against the multi-drug resistant NDM-1 Kp in pneumonia murine.

tered a single i.p. dose of rCST9/rCSTC (500 pg of each/mouse). Both rCST treatment regimens significantly increased survival compared to that in NDM-1 Kp-infected mice alone (p<0.05). Data are presented as mean±SEM, and the asterisk signifies significant differences of p<0.05.

Optimization of PEGylation rCST9: The PEGylation protocol can be optimized and tested on BSA and are currently PEGlyating rCST9 and rCSTC for evaluation in vivo.

Figure 3:
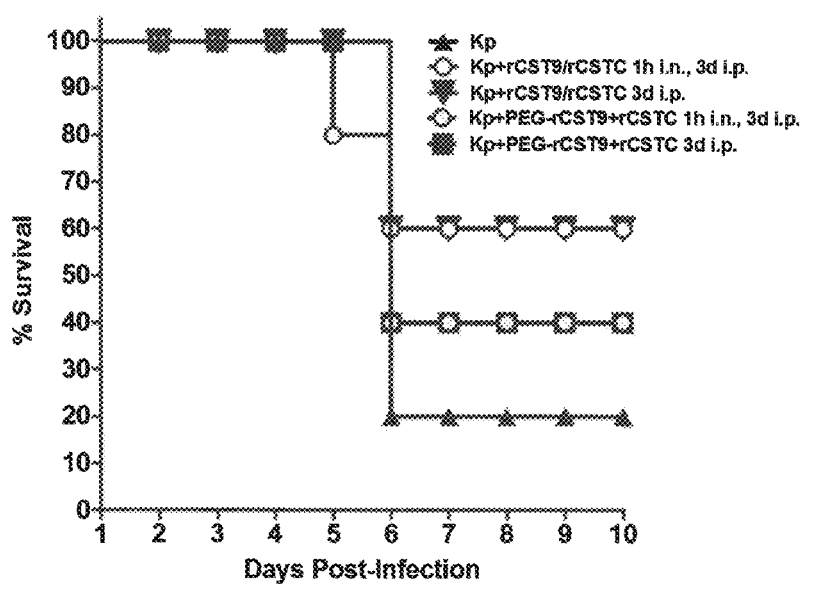

Evaluate lung status following rCST-9 treatment in a mouse model of pneumonia. To evaluate host responses to rCST9/rCSTC, parallel groups of mice (n=4/group) were infected and treated with a combination rCST9/rCSTC (described above) as follows: 1) rCST9/rCSTC was administered i.n. (50 pg of each/mouse) on 1 h PI and i.p (500 pg of each/mouse) on 3 d PI, OR 2) a single i.p. dose of rCST9/rCSTC (500 pg of each/mouse) was given on 3 d PI. Serum, bronchial alveolar lavage fluid (BALF), lungs, liver and spleen were collected on day 5 PI to analyze bacterial load, lung histology and cytokine profiles. FIG. 3 shows the results from pegylation of rCST9, co-administered with rCSTC, did not improve survival outcomes of NDM-1 Kp infected mice. Balb/c mice (n=15 mice/gp) were i.n. infected with an LD90 challenge with NDM-1 Kp and then treated with an i.n. dose of PEG-rCST9/rCSTC (50 pg of each/mouse) on 1 h PI followed by 500 pg of PEG-rCST9/rCSTC/mouse at 3 d PI or mice were administered a single i.p. dose of PEG-rCST9/rCSTC (500 pg of each/mouse) at 3 d PI. PEG-rCST9/rCSTC did not improve the survival of infected

TABLE 1

Cystatin treatment regimens to combat NDM-1 Kp in pneumonia.

| Treatment | Dose per mouse | Route | Administration Pre-infection | Administration Post-infection | increased % survival of Kp LD90 mice |
|---|---|---|---|---|---|
| rCST9 or rCSTC | 50 pg | i.n. | 1 h | | 10%, 20% respectively |
| rCST9 or rCSTC | 500 pg | i.n. | 1 h | | 10% |
| rCST9 or rCSTC | 50 pg | i.n. | | 3 d | 10% |
| rCST9 or rCSTC | 500 pg | i.n. | | 1 h and 3 d | 10% |
| rCST9 or rCSTC | 50 pg | i.p. then i.p. | | 1 h and 3 d | 5% |
| rCST9 and rCSTC | 50 pg, 500 pg | i.n. then i.p. | | 1 d and 3 d | 20% |
| rCST9 and rCSTC | 500 pg | i.p. then i.n. | | 1 d and 3 d | 10% |
| rCST9 and rCSTC | 500 pg | i.p. | | 4 d | 5% |
| rCST9 and rCSTC | 500 pg | i.p. | | 5 d | 0% |
| rCST9 and rCSTC | 500 pg | i.p. | | 1 d and 3 d | 5% |
| rCST9 and rCSTC | 50 pg, 500 pg | i.n. then i.p. | | 1 d and 3 d | 25% |
| rCST9 and rCSTC | 50 pg, 500 pg | i.n. then i.p. | | 1 h and 3 d | 38% |
| rCST9 and rCSTC | 500 pg | i.p. | | 3 d | 35% |

The inventors observed comparable survival rates when Kp infected mice were treated with individual rCST9 or rCSTC. The single i.p. dose of rCST9 or rCSTC at 50 pg/mouse increased survival of Kp infected mice by 15% [Table 1]. However, the combination of rCST9 and rCSTC (rCST9/rCSTC) markedly improved survival compared to individual treatments [Table 1; italicized groups]. FIG. 1 shows the establishment of LD90 NDM-1 Kp pneumonia murine model. Balb/c mice (n=20 mice/group) were intranasally (i.n.) inoculated with various challenge doses of NDM-1 Kp and their survival was observed for 10 d. The LD90 of Kp resulted in $1.82 \times 10^8$ CFU per mouse.

Figure 2:
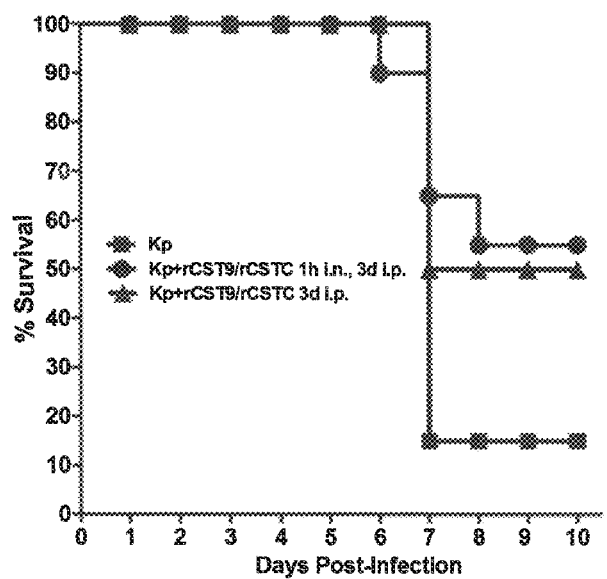
FIG. 2 shows an example of optimal rCST9/rCSTC treatment regimens affords protection against NDM-1 Kp pneumonia. Balb/c mice (n=20 mice/gp) were i.n. infected with NDM-1 Kp ($1.82 \times 10^8$ CFU/mouse) and then treated as follows: mice were given an i.n. dose of rCST9/rCSTC (50 pg of each/mouse) at 1 h PI followed by 500 pg of both rCST9/rCSTC/mouse on the 3 d PI or mice were administered a single i.p. dose of rCST9/rCSTC (500 pg of each/mouse). Both rCST treatment regimens significantly increased survival compared to that in NDM-1 Kp-infected mice alone ($p<0.05$). Data are presented as mean±SEM, and the asterisk signifies significant differences of $p<0.05$.

FIG. 2 shows an example of optimal rCST9/rCSTC treatment regimens affords protection against NDM-1 Kp pneumonia. Balb/c mice (n=20 mice/gp) were i.n. infected with NDM-1 Kp ($1.82 \times 10^8$ CFU/mouse) and then treated as follows: mice were given an i.n. dose of rCST9/rCSTC (50 pg of each/mouse) at 1 h PI followed by 500 pg of both rCST9/rCSTC/mouse on the 3 d PI or mice were adminismice that surpassed rCST9/rCSTC. However, both groups that receive the i.p. administration of rCST9 or PEG-rCST9 in combination with rCSTC on day 3 PI significantly increased survival compared to NDM-1 Kp infected mice (p<0.05). Data are presented as mean±SEM, and asterisk signifies significant differences of p<0.05.

Figure 4:
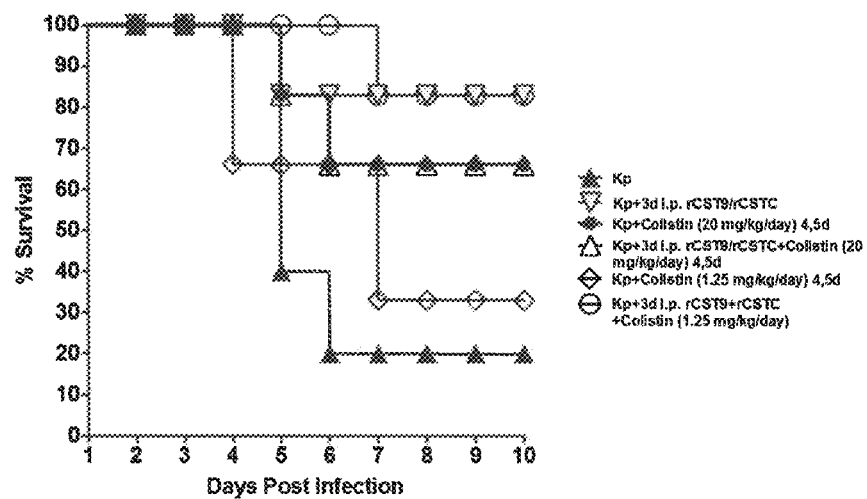

The potential for rCST9/rCSTC treatment to extend the period before successful antibiotic intervention was initiated was determined. For these evaluations, suboptimal doses of colistin were used to determine the extent of protection afforded by rCSTs as well as to minimize side effects/toxicity caused by this antibiotic (n=10 mice/gp). Doses, timing, and route of colistin were chosen based on efficacy studies of colistin in a mouse model of severe, established MDR pneumonia [33] or a very low dose of colistin then adjusted to suboptimal levels for this study. LD90 NDM-1 Kp-challenged mice were treated with the rCST9/rCSTC 3 d i.p. treatment and then given 2 doses of colistin at 20 mg/kg/day or 1.25 mg/kg/day on day 4 and 5 PI. Conversely, rCST treatment administered prior to 1.25 mg/kg/day of colistin 4 and 5 days PI significantly improved survival outcomes in NDM-1 Kp-infected mice (FIG. 4; p<0.05). Interestingly, rCST treatment alone confirmed that the rCST treatment led to an unprecedented improvement in survival of NDM-1 Kp-infected mice compared to the low dose of colistin alone and NDM-1 Kp controls (FIG. 4; p<0.05). These results showed that rCST treatment extended the period before antibiotic intervention is initiated and importantly rCST treatment works synergistically with a dramatically lower, less toxic dose of colistin to combat pneumonia.

These data showed that the combination of rCST9 and rCSTC administered to the primary sight of infection (i.n.) prevented lung damage following Kp infection. More, rCST9 and rCSTC given i.p. modulated both systemic Kp as well as lung inflammation resulting in significantly improved survival.

Evaluate alternative dosages of rCST9 and PEG rCST9. The inventors used 1000 pg/mouse of single and combined treatments of rCST9/rCSTC administered at the optimized time(s) 1 h and/or 3 d PI as well as 4 d and 5 d PI using i.n. and/or i.p route(s).

Combined therapies of rCST9 can be evaluated with current antimicrobial agents to minimize ALI/ARDS leading to improved survival (e.g. increase in survival of 10-15%) that surpasses a single therapeutic treatment in an experimental mouse model of bacterial pneumonia, e.g., minimizing ALI/ARDS leading to improved host survival.

Evaluation of combined treatments. Colistin is the one antibiotic NDM-1 Kp 2146 is sensitive to, therefore, the inventors can use the system disclosed hereinabove to evaluate suboptimal dosages of colistin in the two optimized LD90 Kp-rCST9 and rCSTC models. Specifically, colistin is administered at a suboptimal dose on 4 d or 5 d PI/cystatin treatment. The timing of colistin treatment can also be adjusted to optimize results.

Figure 5A:
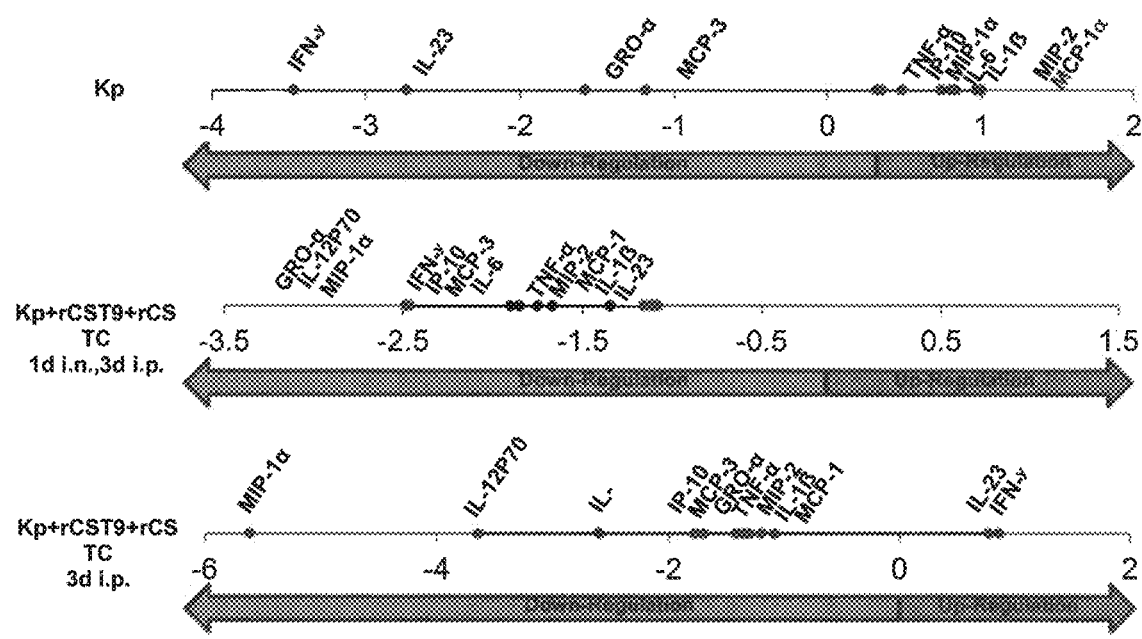

FIG. 5A shows that rCST9/rCSTC treatment modulated inflammatory responses and preserved lung integrity in a mouse model of pneumonia. Balb/c mice (n=6 mice/gp) were i.n. infected with NDM-1 Kp ($1.82 \times 10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Serum was collected and lungs, livers, and spleens were harvested at 5 days PI. Fold change in the overall cytokine levels in the serum (FIG. 5A) of rCST treated mice were decreased compared to untreated in NDM-1 infected mice.

Figure 5B:
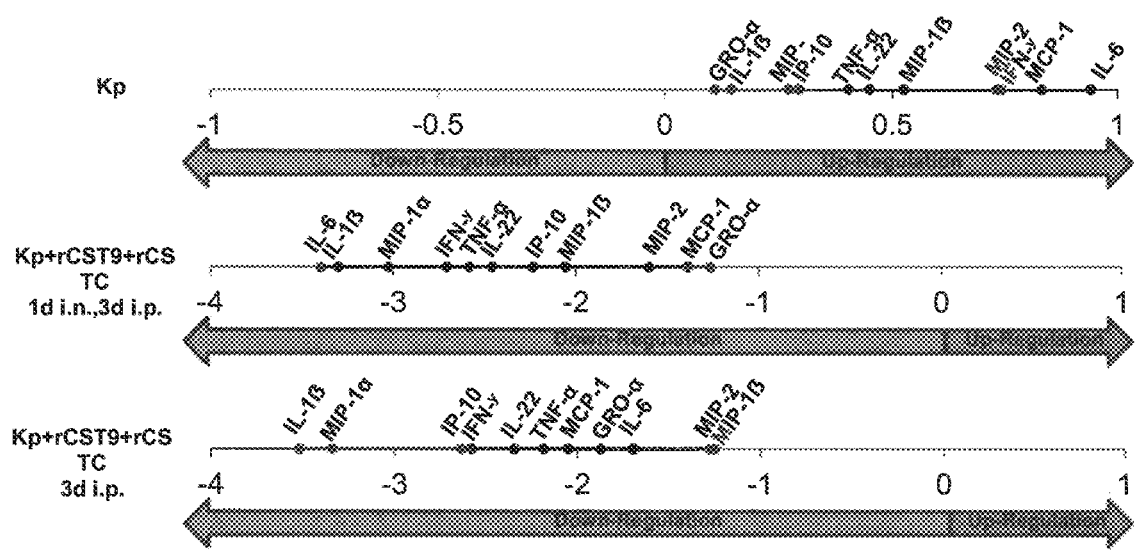

FIG. 5B shows that rCST9/rCSTC treatment modulated inflammatory responses and preserved lung integrity in a mouse model of pneumonia. Balb/c mice (n=6 mice/gp) were i.n. infected with NDM-1 Kp ($1.82 \times 10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Serum was collected and lungs, livers, and spleens were harvested at 5 days PI. Fold change in the overall cytokine levels in the lungs (FIG. 5B) of rCST treated mice were decreased compared to untreated in NDM-1 infected mice.

Figure 5C:
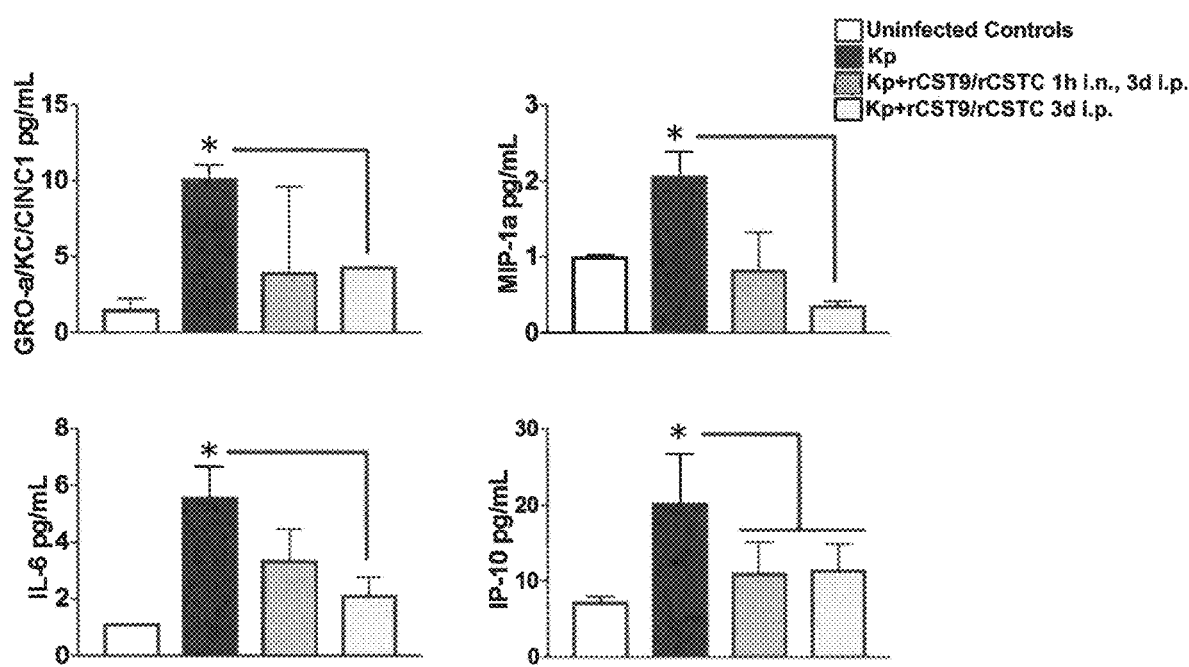

FIG. 5C shows that rCST9/rCSTC treatment modulated inflammatory responses and preserved lung integrity in a mouse model of pneumonia. Balb/c mice (n=6 mice/gp) were i.n. infected with NDM-1 Kp ($1.82 \times 10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Both rCST9/rCSTC treatments modulated cytokine secretion in the serum (FIG. 5C).

Figure 5D:
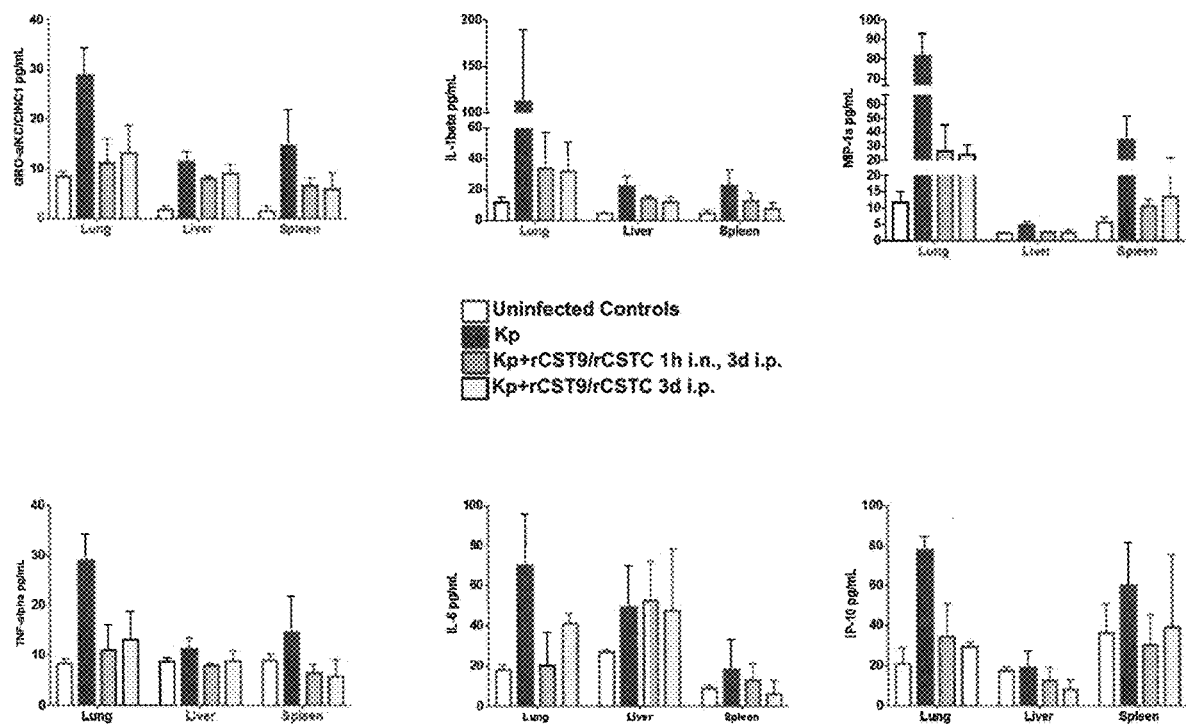
Figure 5E:
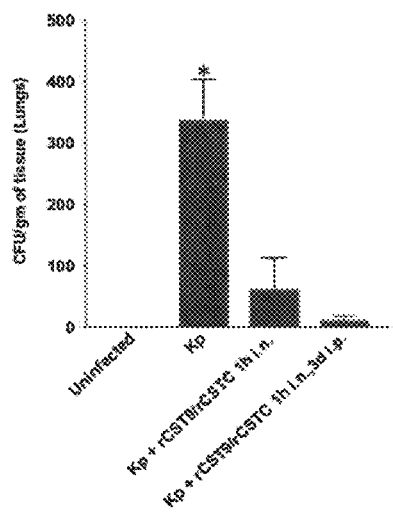
Figure 5F:
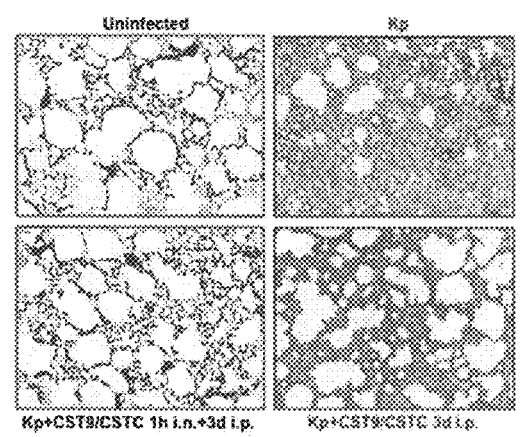

FIG. 5D shows that rCST9/rCSTC treatment modulated inflammatory responses and preserved lung integrity in a mouse model of pneumonia. Balb/c mice (n=6 mice/gp) were i.n. infected with NDM-1 Kp ($1.82 \times 10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Both rCST9/rCSTC treatments modulated cytokine secretion in all tested organs (FIG. 5D).

Figure 5G:
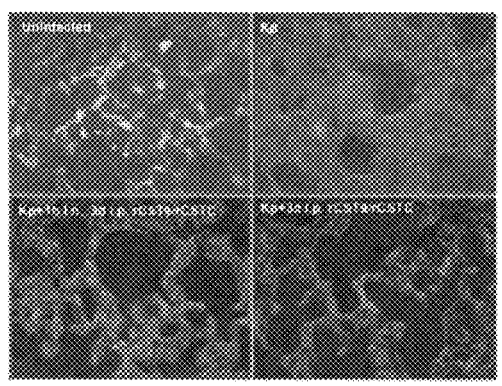
Figure 5H:
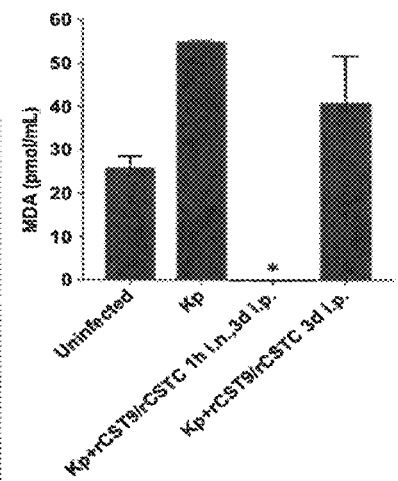

FIGS. 5E to 5H shows that rCST9/rCSTC treatment modulated inflammatory responses and preserved lung integrity in a mouse model of pneumonia. Balb/c mice (n=6 mice/gp) were i.n. infected with NDM-1 Kp ($1.82 \times 10^8$ CFU/mouse) and then treated with an i.n. dose of rCST9/rCSTC (50 pg of both/mouse) at 1 h PI followed by 500 pg of each rCST9/rCSTC/mouse at 3 d PI or mice were administered a single i.p. dose of rCST9/rCSTC (500 pg of each/mouse). Both rCST9/rCSTC treatments significantly reduced bacterial burden in the lungs (E). Lung histology (H&E; 40× mag) from the same treated and/or infected mice showed that both rCST treatment regimens minimalized lung pathology caused by NDM-1 Kp (FIG. 5F). rCST treatment reduced apoptotic cells compared to untreated/infected mice (FIG. 5G). MDA detection in the lungs was significantly decreased in rCST-treated and infected mice (FIG. 5H). Data are presented as mean±SEM, and asterisk signifies significant differences of p<0.05.

Figure 6A:
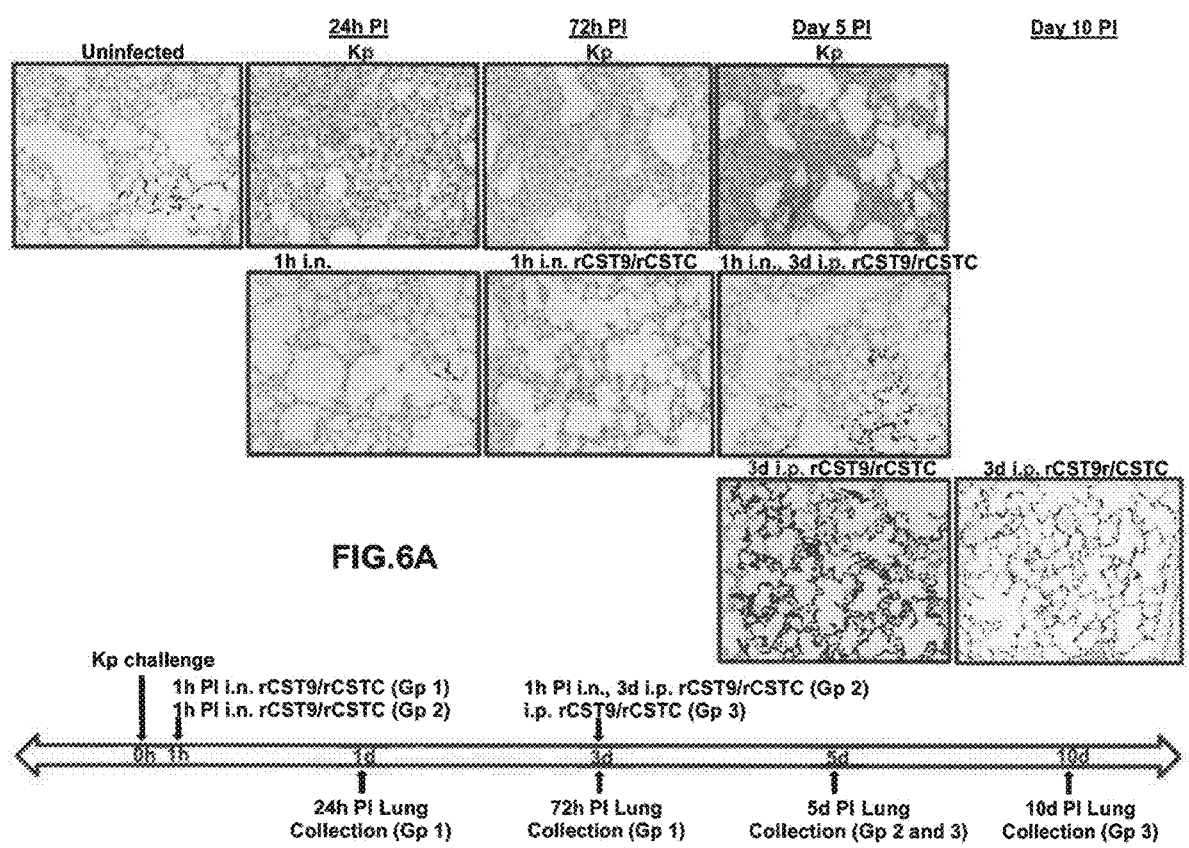
FIG. 6B shows histolopathological scoring of the lungs (0=no significant changes, 1=slight damage, 2=mild to moderate damage, 3=moderate to severe damage and 4=severe damage in each of the three categories. Results showed that cystain treatments significantly decreased lung damage compared to corresponding time points of infected mice alone. Mice receiving rCSTs at 3 d PI and lungs collected from survivors at 5 and 10 d PI had mild to no damage compared to infected mice alone groups (*p<0.05 and **p<0.01 respectively). The scoring results were expressed as SQS (mean±SEM).
FIG. 6C shows likewise, lungs from the same rCST-treated and infected groups showed markedly fewer apoptotic cells at 24 and 72 h PI. All images are representative of the analysis of 4-6 sections of each mouse.
Figure 6B:
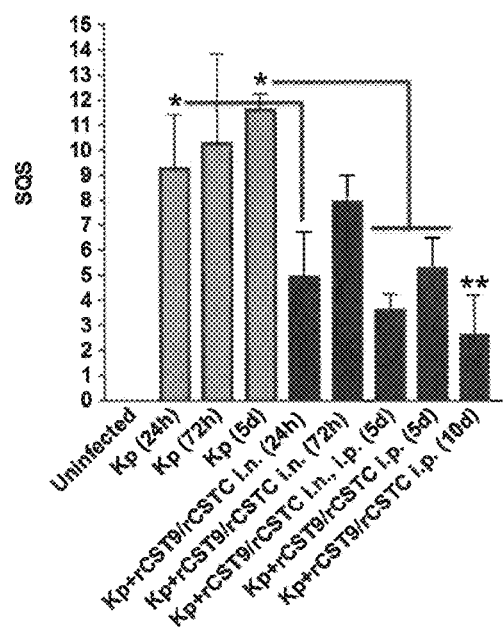
Figure 6C:
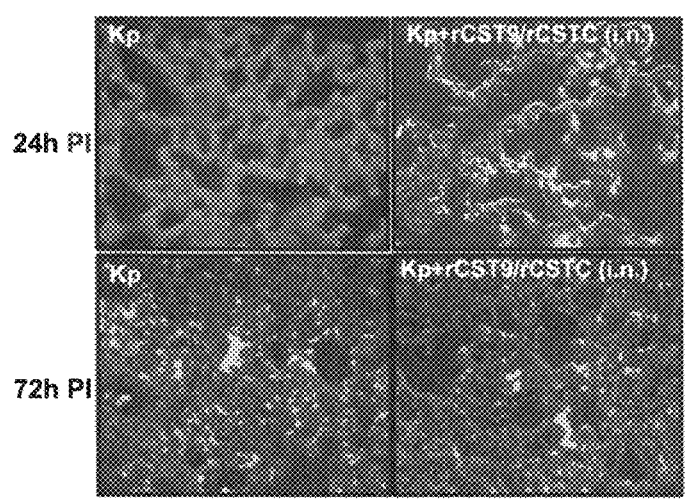

FIGS. 6A to 6C show that rCST treatments preserved lung integrity and prevented long-term lung damage. Balb/c mice (n=4 mice/gp) were i.n. infected with NDM-1 Kp ($1.82 \times 10^8$ CFU/mouse) and then treated with an i.n. dose of rCST9/rCSTC (50 pg of each). The lungs were harvested at 24 h and 72 h PI. A parallel group of mice were infected and treated i.n./i.p. or i.p with rCST9/rCSTC as described herein, and then lungs were harvested on 5 and 10 d PI. Serial sections of the lung were analyzed for histology (40× mag) and apoptosis by using the TUNEL assay with DAPI to stain cell nuclei. FIG. 6A shows the i.n. administration of rCST9/rCSTC to infected mice markedly diminished immune cell infiltration into the lungs and edema at 24 h and 72 h PI compared to high cellularity and signs of hemorrhaging and edema in the lungs of untreated, infected mice. Further, lungs from our two optimal rCST9/rCSTC treatments on 5 d and 10 d PI prevented long-term lung damage and showed resolution of inflammation. FIG. 6B shows histolopathological scoring of the lungs (0=no significant changes, 1=slight damage, 2=mild to moderate damage, 3=moderate to severe damage and 4=severe damage in each of the three categories. Results showed that cystain treatments significantly decreased lung damage compared to corresponding time points of infected mice alone. Mice receiving rCSTs at 3 d PI and lungs collected from survivors at 5 and 10 d PI had mild to no damage compared to infected mice alone groups (*p<0.05 and **p<0.01 respectively). The scoring results were expressed as SQS (mean±SEM). FIG. 6C shows likewise, lungs from the same rCST-treated and infected groups showed markedly fewer apoptotic cells at 24 and 72 h PI. All images are representative of the analysis of 4-6 sections of each mouse.

Figure 7A:
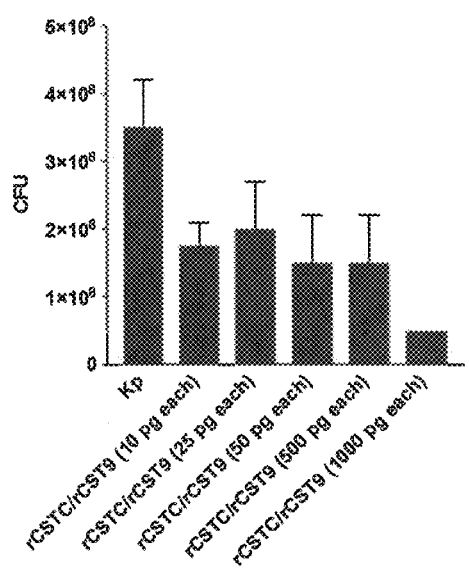
FIGS. 7A to 7C show the anti-microbial properties of rCST9/rCSTC against NDM-1 Kp. rCST9/rCSTC inhibited the metabolic activity and growth of NDM-1 Kp. The 50, 500, and 1000 pg of rCST9/rCSTC decreased metabolic activity (FIG. 7A), bacterial replication (FIG. 7B) and growth (FIG. 7C) NDM-1 Kp ($1\times10^6$ CFU/mL) following a 6 h incubation. Data are presented as mean±SEM, and asterisk signifies significant differences of $p<0.05$ compared to all other groups.
Figure 7B:
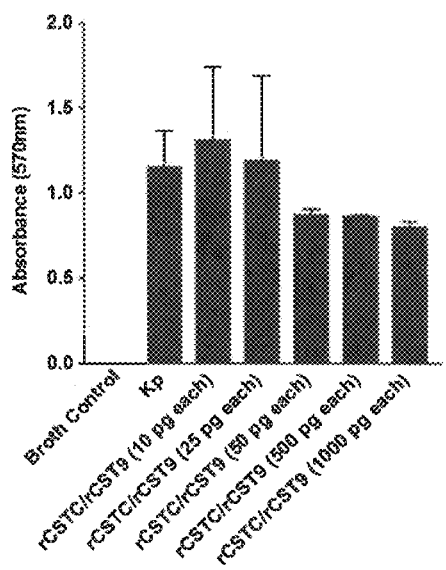
Figure 7C:
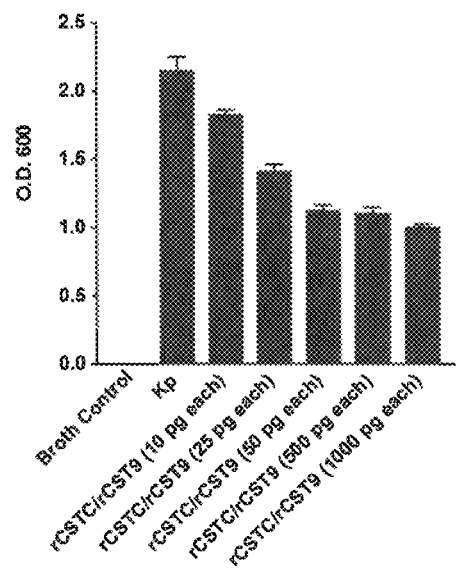

Anti-microbial activity of rCST9/rCSTC against NDM-1 Kp. Past studies also revealed a direct antimicrobial activity of rCSTs. To address this directly, PrestoBlue® was used to determine the viability of rCST9/rCSTC-treated NDM-1 Kp based in the reagents rapid reduction by metabolically active bacteria. These findings revealed that 50, 500, and 1000 pg of rCST9/rCSTC decreased the viability/metabolic activity of $1\times10^6$ CFU/mL of NDM-1 Kp during the 6 h incubation compared to untreated NDM-1 Kp and NDM-1 Kp incubated with 10 or 25 pg of rCSTs (FIG. 7A; p<0.05). Further, at 6 h post-incubation, optical density (O.D.) readings and CFUs showed bacterial growth inhibition of NDM-1 Kp incubated with all tested doses of rCSTs compared to NDM-1 Kp alone (FIG. 7B and FIG. 7C; p<0.05). The most substantial decrease in bacterial growth occurred with 50, 500, and 1000 pg of rCSTs compared to lower doses of 10 and 25 pg of rCSTs (FIGS. 7A-C). These results showed that rCST9/rCSTC directly decreased the viability and growth of NDM-1 Kp.

Assess the ability of prophylactic rCST9 to provide a longer window for initiation of antimicrobial treatment leading to prolonged survival (>10-15%) compared to post-treatment alone. As shown above, rCST9's ability to extend the period before antimicrobial treatment was shown against NDM-1 Kp pneumonia.

These findings demonstrate that a single i.n. dose of 50 pg of rCST9 or rCSTC administered 1 h prior to an LD90 dose of i.n. Kp increased survival compared to Kp infected alone [Table 1]. This prophylactic cystatin treatment regime as well as the combination of rCST9/rCSTC followed by colistin 3 d or 5 d PI to evaluate improvement in survival as well as prolonged survival can also be determined. The prophylactic single or combined cystatin doses should increase survival >15% compared to the LD90 Kp model.

The protective effects of rCST9 against an NDM-1 Kp infection in mice can be translated to a human lung model necessary for translation to drug development in patients. These studies allow for more accurate, clinically relevant assessment of rCST9 to better predict its behavior in patients and will begin to evaluate the PK and potential toxicity of rCST9.

As such, it is possible to evaluate the protective effects of rCST9 against NDM-1 Kp infection in an improved human lung cell model. A new cystatin protein purification protocol using a loose Nickel resin allowing for cleaner purification and milligrams of protein isolation can also be used.

The ability of bacterial organisms to acquire MDR genes is on the rise, making infections caused by MDR pathogens difficult to treat with traditional antibiotics. Therefore, the development of novel, effective therapeutic inventions for these deadly infections is imperative. Herein, it is demonstrated that two human cysteine proteinase inhibitors, known as cystatin 9 and cystatin C, are immunomodulators of inflammation caused by deadly pathogens. This study showed that rCST9 and rCSTC worked synergistically, and in a multi-faceted manner, to modulate excessive, damaging inflammatory responses in pneumonia caused by MDR NDM-1 Kp. Therapeutic efficacy was established using two different rCST9/rCSTC treatment regimens in mice challenged with an LD90 dose of MDR NDM-1 Kp. Post-infection rCST treatment at the primary site of infection (lungs) as well as a single systemic treatment (i.p.) enhanced bacterial clearance and significantly improved survival. Further, it was found that the established rCST9/rCSTC treatment regimens were not toxic or harmful to the host.

Initially, rCSTC was used as a comparative control for rCST9 and then, unexpectedly, discovered that treatment with the combination of rCST9 and rCSTC worked synergistically to combat deadly MDR Kp pneumonia. These efficacy studies determined that low doses and as few as one treatment of rCST9/rCSTC significantly modulated otherwise excessive cytokine secretion to a beneficial level and enhanced bacterial clearance, allowing the host to successfully fight and ultimately resolve the infection, resulting in an unprecedented improvement in survival. Surprisingly, systemic administration of a single i.p. dose of rCST9/rCSTC (500 pg each) after the establishment and systemic dissemination (3 d PI) of the infection remarkably improved survival outcomes at levels that were equivalent to the dual i.n./i.p. treatment regimen. Moreover, the single rCST9/rCSTC dose tempered damaging pulmonary and systemic cytokine secretion that decreased lung pathology (e.g. MDA and apoptosis). In fact, in rCST treated mice the lung histology was normal with no signs of long-term damage by 10 d PI.

To capitalize on the protective effects of the small, optimal doses of rCSTs, rCST9 was pegylated in an effort to potentially improve its bioavailability in NDM-1 Kp-infected mice. Pegylation is the method of covalently attaching polyethylene glycol to a target, small molecule to improve therapeutic efficacy and pharmacokinetics by enhancing the bioavailability, stability and half-life of small-molecule drugs in vivo [34, 35]. Despite successful pegylation, co-administered PEG-rCST9 and rCSTC actually showed decreased survival outcomes. These results are consistent with testing of higher or more frequent rCST9/rCSTC doses that did not improve survival against NDM-1 Kp pneumonia (data not shown). Additional studies of the PEG-rCST9/rCSTC at lower doses or different combinations will be required to fully appreciate the impact of pegylation. In one non-limiting example, a low-dose, 2 route delivery course was optimal and provided a solid foundation of pharmacokinetic and pharmacodynamic results for immunotherapeutic interventions against pneumonia.

Treatment of pneumonia attributed to NDM-1 Kp remains challenging because of the acquired resistance to most commercially available antibiotics as well as the pathogen's ability to survive for extended periods on environmental surfaces, factors that enhance person-to-person transmission [16, 17, 20, 21, 24]. Combination antibiotic therapy is routinely implemented to treat NDM-1 Kp pneumonia, but these antibiotic poly-treatments are typically accompanied by serious side effects due to the high doses necessary to fight the infection. The NDM-1 Kp strain used in these studies is sensitive to colistin, which is a mixture of polymyxins, specifically polymyxin E, that is considered a last resort treatment for MDR Gram-negative pathogens due to kidney toxicity [36]. Therefore, optimal rCST treatments were accompanied by 20 mg/kg/day or 1.25 mg/kg/day of colistin to determine the extent of protection afforded by rCSTs before antibiotic intervention. Administration of 20 mg/kg/day of colistin 2 times/day for 2 d following optimal rCST treatments did not increase survival outcomes that exceeded the single, low dose of rCST alone. However, rCST treatment given prior to the administration of a low, suboptimal dose of 1.25 mg/kg/day of colistin on days 4 and 5 PI significantly improved survival outcomes compared to colistin alone. These results showed that the administration of suboptimal antibiotic therapy allowed enhanced efficacy in the presence of rCSTs that will likely minimize side effects/toxicity caused by the antibiotic, however, additional studies will be required to address this question. It is important to note that neither of the antibiotic doses surpassed protection afforded by the rCST monotherapy.

Finally, these findings showed that 50, 500 and 1000 pg of rCST9/rCSTC directly inhibited NDM-1 Kp metabolic activity and growth. 1000 pg of the rCSTs inhibited NDM-1 Kp metabolic activity and growth nearly equivalent to optimal rCST in vivo doses of 50 and/or 500 pg, the rCST 1000 pg dose did not provide significant protection in the murine model of pneumonia (data not shown). This invention describes the effects of rCST9 [15] and/or rCSTC on deadly MDR bacterial pathogens both in vitro and in vivo for the first time.

Due to the numerous strains of rapidly evolving MDR pathogens, there is an urgent need to develop alternative therapeutic agents to treat these deadly human infections. These findings reveal the multifaceted synergistic, immune-regulatory functions of rCST9/rCSTC. Herein, it is shown that the exogenous co-administration of human rCST9/rCSTC preserved lung integrity, modulated local and systemic cytokine secretion, enhanced anti-bacterial immune responses, and bacterial clearance of MDR NDM-1 Kp pneumonia. These findings showed that a single, low-dose administration of rCST9/rCSTC afforded unprecedented protection without toxic side effects. These findings demonstrate that rCST9/rCSTC provided broad-spectrum protection against pneumonia caused by MDR NDM-1 Kp, and modulated inflammation in multifaceted and unpredicted ways.

Human recombinant CSTC and CST9. Recombinant human Cystatin C was purchased from R&D Systems (Minneapolis, MN) and rCST9 was purchased from American Research Products, Inc™ (Waltham, MA).

Bacteria preparation. The MDR New Delhi metallo-beta-lactamase-1 (NDM-1) producing *Klebsiella pneumoniae* BAA-2146™ was purchased from ATCC and expanded for 18 hours in 10 mL of brain heart infusion (BHI) broth while shaking at 37° C. The overnight culture was pelleted by centrifugation and then suspended in PBS. Serial dilutions were performed to obtain the desired concentration. Ten-fold dilutions were plated on BHI agar to confirm experimental dosage.

Pegylation of rCST9. In order to generate an N-terminal mono-PEGylated (PEG) human rCST9 protein, purified rCST9 was incubated with 20 kDa Methoxy PEG Propionaldehyde (M-ALD-20K; Jenkem Technology, Beijing, China) and sodium cyanoborohydride (Sigma-Aldrich, St. Louis, MO) at a molar ratio of 1:8:80 in 50 mM sodium acetate buffer (pH 4.5). After 46 hrs incubation at room temperature, the mixture was loaded onto a Superdex 75 column (1.6 cm×60 cm, GE Healthcare, USA) equilibrated with Hank's Balanced Salt Solution (HBSS buffer). Proteins were subsequently eluted and fractionated by using HBSS at a flow rate of 2 mL/min and detected by the absorbance of 280 nm. Fractions containing the PEGylated rCST9 were further identified and protein content profiled by SDS-PAGE analysis.

Mouse model of pneumonia and CST treatments. Eight-week old female Balb/c mice weighing between 21 and 24 grams (Jackson Laboratories) were housed in an Association for Assessment and Accreditation for Laboratory Animal Care (AAALAC)-approved housing facility and permitted to adjust to their environment for 7 d prior to procedures, receiving free access to food and water throughout the study. All procedures were approved by the University of Texas Medical Branch IACUC and performed humanely with minimal suffering. We established an LD90 model of pneumonia by anesthetizing mice (n=15-20 mice/gp) with sodium pentobarbital and then challenging them with an i.n. dose of $1.82 \times 10^8$ CFU/mouse of NDM-1 Kp as previously described [15, 42]. One hour PI, mice were administered an i.n. dose of rCST9/rCSTC (50 pg of each) and then, this group of mice was given an i.p. injection of rCST9/rCSTC (500 pg of each) 3 d PI. A parallel group of infected mice received only a single i.p. dose of rCST9/rCSTC, PEG-rCST9/rCSTC (500 pg of each), or PEG-rCST9 (500 pg) alone 3 d PI. NDM-1-Kp infected mice alone or uninfected mice served as controls. Survival was observed up to 15 days post treatment. Additional groups (n=4 mice/group) of infected and CST-treated mice were euthanized at selected time points (24 h, 72 h, 5 and/or 10 d PI) to harvest lungs. Additional groups were treated with i.n. rCSTs (50 pg of each) as described above but they were euthanized at 30 min, 1 h and 3 h to collect lungs for the quantification of lipid peroxidase by-product, known as malondialdehyde (MDA), as described below.

Additional groups of mice (n=15 mice/group) were treated with the optimal CST treatment regimens of an i.n. dose of rCST9/rCSTC (50 pg of each), followed by an i.p. injection of rCST9/rCSTC (500 pg of each) 3 d PI or the single i.p. dose of rCST9/rCSTC (500 pg of each). At 4 d PI, mice were given 2 separate i.p. injections of colistin (JHP Pharmaceuticals, LLC; colistimethate sodium; 20 mg/kg/mouse or 1.25 mg/kg/day) 8 h apart for 2 d. Survival was observed for 15-20 days.

Lung histology, apoptosis, lipid peroxidation, and bacterial burden. Following collection, organs were weighed, then a small portion of the lungs was fixed and processed for hematoxylin and eosin (H&E) staining. A semi-quantitative scoring system was employed to the lung sections collected at 24 h, 72 h, 5 d and 10 d PI (FIGS. 6A and B). The entire lung section from each condition was analyzed under the following categories: structural abnormalities/congestion, hemorrhaging and cellularity. A lung section from each condition was analyzed in triplicate from 3 individual subjects. Each lung section was given a score ranging from 0-4, whereby 0=no significant changes, 1=slight damage, 2=mild to moderate damage, 3=moderate to severe damage and 4=severe damage in each of the three categories. The semi-quantitative score (SQS) is expressed as the sum of the scores from all three categories. The scoring results were expressed as SQS (mean±SEM).

Apoptotic cells were identified from parallel lung sections by a TUNEL assay using an in situ cell death detection kit (Trevigen) as per the manufacturer's instructions. Nuclei were stained with SlowFade Diamond AntiFade Mountant with DAPI (Invitrogen). Remaining lung materials were homogenized in 1 mL of PBS. Aliquots of lung tissue homogenates were analyzed via a malondialdehyde (MDA) assay kit (Cell Biolabs Inc.), using the manufacturer's instructions, to detect tissue damage induced by oxidative stress. For each lung, 10% (100 ul) of the gravity clarified homogentate was plated on BHI agar to determine the bacterial burden. Bacterial counts were calculated and expressed as CFU/gram of tissue.

Cytokine profile analysis and ELISA kits. Homogenized tissue supernatants and serum (50 ul samples) were analyzed by ProcartaPlex® Mouse Cytokine/Chemokine (Affymetrix) to quantify cytokine production. Samples were processed per the manufacturer's instruction on a Bio-Plex200 instrument (Bio-Rad).

In vitro bacteria viability and growth assay. As a measure of NDM-1 Kp viability, aliquots were treated with Prestoblue® cell viability reagent (Invivogen) following exposure to CSTs. Briefly, $1 \times 10^6$ CFU/mL of NDM-1 Kp were incubated with 10, 25, 50, 500 or 1000 pg of rCST9/rCSTC at 37° C. for 6 hours. Following incubation, 10 L of Prestoblue® reagent was added to each sample and incubated for 1 h before quantification of cell viability via absorbance at 570-600 nm measurement (Bio-Tek; Epoch Model). Parallel aliquots of rCST treated cultures or untreated cultures were used to determine the optical density of the resulting bacterial cultures via spectrophotometry (O.D. 600 nm). Additionally, 100 µL of cultures were plated on BHI plates to quantify colony-forming units (CFU) following an overnight incubation at 37° C. These studies were performed as per a study by Dr. Coban [43] and according to CLSI recommendations.

Statistical Analysis. Where appropriate, results are reported as mean±SEM of two-to-three independent experiments. Analysis of numerical data was determined by one-way ANOVA and Student's t-test using Prism v7.0c software (Graph Pad, San Diego, CA). Survival data were analyzed by log-rank analyses with Welch's corrections using Prism software (GraphPad). Differences were considered statistically significant when the p value was <0.05.

Example 2. Cystatins Modulate Dysregulated Gut-Derived Inflammation and Preserve the Gut Microbiome in a Mouse Model of Sepsis and Thermal Injury Dysregulated inflammation and sepsis following thermal injury causes gut dysbiosis leading to the leakage of gut contents into the circulation and lymphatics. Maintaining gut barrier integrity can decrease and/or prevent damaging inflammation and sepsis following thermal injury. Example 1 shows that co-administration of human recombinant cystatin 9 (rCST9) and cystatin C (rCSTC) is an immunotherapy that modulates excessive inflammation caused by a lethal bacterial infection. Next, the inventors determined whether rCST9/rCSTC improves survival outcomes following thermal injury via the modulation of dysregulated systemic inflammation and maintain the gut microbiome.

Mice were intraperitoneally (i.p.) challenged with $1 \times 10^7$ CFU of an intestinal isolate E. coli (EC) and 1000 ng of flagellin then treated i.p. with 500 pg rCST9 and/or 50 pg rCSTC followed by a 30% full-thickness thermal injury (30% TBSA). Survival was observed for 10 days. Additional groups of infected, rCST treated and/or thermally injured mice were euthanized at 24 and 48 h post-thermal injury to collect serum and harvest intestinal samples. Cytokines were quantified in the serum and analysis of the gut microbiome.

It was found that rCSTs afforded 100% survival in infected/thermal-injured mice compared to burn only or mice treated with individual rCST (p<0.05). Further, rCST9/rCSTC modulated systemic MCP-1, MCP-3, IP-10, IL-6, and GRO-α/KC at 24 h post-infection and thermal injury. The gut microbiome in the mice receiving both rCST9/rCSTC was overwhelmingly Lachnospiraceae spp, which has been reported to maintain intestinal barrier functions.

Gut-derived inflammation and/or sepsis is one of the leading causes of morbidity and mortality in thermally injured patients. The human gut contains approximately $1 \times 10^{12}$ bacteria (1). These communities of commensal bacteria are known as the gut microbiome and, under normal circumstances, they live in a symbiotic relationship with the host if confined to the intestine. However, during trauma, such as thermal injury, commensal bacteria and their products can translocation from the intestine into the general circulation where they can induce dysregulated, damaging inflammation leading to multiple organ failure, morbidity and/or mortality (2). The on-set of inflammation is rapid, and can cause a post-injury septic response (3).

Among the various products of Gram-negative bacteria that can stimulate inflammation, gut-derived or otherwise, are lipopolysaccharides (LPS) and flagellin. Flagellin is the primary protein that makes up the flagella structure (4, 5). However, the flagella can be released or break free from the bacteria liberating the flagellin from the flagella filament. The free flagellin is now able to bind to its receptor, toll-like receptor 5 (6) and subsequently induce inflammation (7). We have shown that following thermal injury, gut-derived flagellemia can develop whereby high levels of flagellin work synergistically with gut-derived bacteria, specifically the gut isolate E. coli (EC) 083:H1, to disrupt the gut microbiota, damage the intestinal barrier and cause intestinal and systemic inflammation (8). The inventors, and others, have demonstrated that following burn injury there are significant alterations of the gut microbiota that contribute to the severity of sepsis. For example, one recent clinical research report found that the pathogenic changes in the gut microbiota induced by a severe burn injury are reversed in those patients that recover, suggesting a link between the restoration of normal, healthy microbial populations with survival (12, 13). Therefore, it has been hypothesized that maintaining a healthy gut microbiota and intestinal barrier function is crucial to patient survival outcomes.

The problem is that current agents, such as antibiotics used to treat inflammation and/or sepsis following burn injury, can have toxic side effects due to the high doses and duration of treatment necessary to combat the rapid on-set of inflammation (12). Further, antibiotics can cause and/or contribute to gut dysbiosis by eliminating some organisms while allowing others to overgrow thus disrupting the symbiotic relationship between the resident bacterial communities and the host (13). Therefore, it is imperative that new treatments are developed to stand-alone or accompany less toxic doses of traditional methods to treat inflammation and sepsis.

As shown in Example 1, it was discovered that human recombinant (r) cystatin proteins, known as cystatin 9 (rCST9) and/or cystatin C (rCSTC), modulate dysregulated, damaging inflammation and afforded unprecedented protection against deadly Tularemia (14) and multidrug-resistant (MDR) pneumonia induced by New Delhi metallo-beta-lactamase-1 (NDM-1) producing Klebsiella pneumoniae (15). These proteins are members of the type II family of cystatins that are cysteine protease inhibitors and are found in all bodily compartments at various concentrations (16, 17). Although CST9 and CSTC are homologous and have similar functions of inhibiting cathepsins, maintaining the homeostasis of tissue remodeling and regulating metalloproteinases, they differentially modulate proteins within these host systems. Therefore, CSTs do not have a global function, their functions are distinct from one another and, in fact, each individual cystatin is protease specific (16, 18). As a therapy, rCST9 and rCSTC administered as a single picogram range dose preserved lung integrity, decreased bacterial load and promoted beneficial immune responses that subsequently led to significant improvement in survival outcomes against lethal MDR NDM-1 pneumonia compared to the individual treatment of rCST9 or rCSTC (15).

Thus, the present inventors determined whether rCST9/rCSTC treatment modulates immune responses to gut-derived inflammation and sepsis as well as stabilizing the gut microbiome leading to improved survival following burn injury. Previously generated gut samples from normal and burn only mice, as previously published (8), were used to compare to rCST treatments.

Ultrapure Salmonella typhimurium flagellin was purchased from Invivogen (San Diego, CA). The enteric E. coli (EC) 083:H1 strain was a generous gift from Dr. Alexander Swidsinki (Charite Hospital, Germany). Briefly the bacteria was inoculated into 10 mL of Brain Heart Infusion (BHI)

broth incubated at 37° C. shaking overnight and then centrifuged, and pellet was resuspended in 10 mL of sterile phosphate-buffered saline (PBS). Bacteria culture was diluted to the desired experimental concentration using serial dilutions followed by the authenticity and confirmation of experimental concentrations by plating the dilutions on BHI agar plates and quantifying CFUs as previously published (8).

Human recombinant CSTC was purchased □from R&D Systems (Minneapolis, MN) and human recombinant CST9 was purchased from American Research Products, Inc. (Waltham, MA).

Female Balb/c mice (n=6 mice/group), weighing 19-21 grams (Jackson Laboratories), were housed in a facility approved by the Association for Assessment and Accreditation for Laboratory Animal Care (AAALAC). Mice were allowed to adjust to their environment for at least seven days prior to the study and given access to food and water throughout the entire study. All animal procedures were approved by University of Texas Medical Branch IACUC and performed humanely with minimal suffering. Briefly, mice were shaved dorsally the morning of experimentation as previously described (8). The mice were given an i.p. challenge of 1000 ng of flagellin and $1\times10^7$ CFU/mouse of EC 083:H1 and then treated with 500 pg of rCST9 and/or 50 pg of rCSTC. Immediately following treatment, mice were anesthetized with pentobarbital (Nembutal) and subjected to a 30% total body surface area (TBSA) burn injury. Groups are as follows: 1) EC/flagellin challenged and burned alone, 2) EC/flagellin challenged, treated with rCST9 and burned, 3) EC/flagellin challenged, treated with rCSTC and burned, or 4) EC/flagellin challenged, treated with rCST9 and/or rCSTC and burned. Mice were resuscitated with an i.p. injection of 1 mL of Lactated Ringer's solution and allowed to recover on a heating pad until fully awake and moving about the cage. Survival was observed for 10 days post-infection.

Parallel groups of mice as described above were euthanized at 24 and 48 h post-burn. Sera were collected via cardiac puncture and cytokines were quantified in the sera serum (50 ul samples) were analyzed by ProcartaPlex® Mouse Cytokine/Chemokine (Affymetrix) to quantify cytokine production. Samples were processed per the manufacturer's instruction on a Bio-Plex200 instrument (Bio-Rad).

Gut samples were harvested at 24 and 48 h from the same 4 mouse groups euthanized to collect sera as described above. As we reported in a previous publication (8), briefly, approximately 3 mm$^3$ pieces of the intestine (close to the cecum) were sterilely harvested from each mouse. For gut microbiome analysis, DNA from intestinal samples was extracted from samples lysed in MagNA Pure DNA Tissue Lysis Buffer followed by automated extraction on a MagNA Pure 96 platform (Roche). The isolated DNA was amplified using a panel of five "universal" primer pairs (Ion Xpress Barcodes) that created overlapping 400 bp DNA fragments covering 95% of the bacterial 16S rDNA. Barcoded amplimers were mixed at equimolar ratios and then subjected to Ion Torrent NGS (Thermo Scientific). Average read length was >300 bases with sequence generated from both strands. Reads were filtered and binned according to Ion Xpress barcode with Ion Torrent Suite software (v 4.0.2). Sequencing reads were then further processed using Galaxy software where each barcode was trimmed to remove the primer sequence. The 16S sequences were compared to the SILVA database using bowtie 2 software to yield species or genera level matches to return the hit-rate. Where multiple calls to the same genera were made the number of hits were added accordingly. Hit rates were converted to percentage of total to give an overall ratio of the sequenced microbiome.

Figure 8:
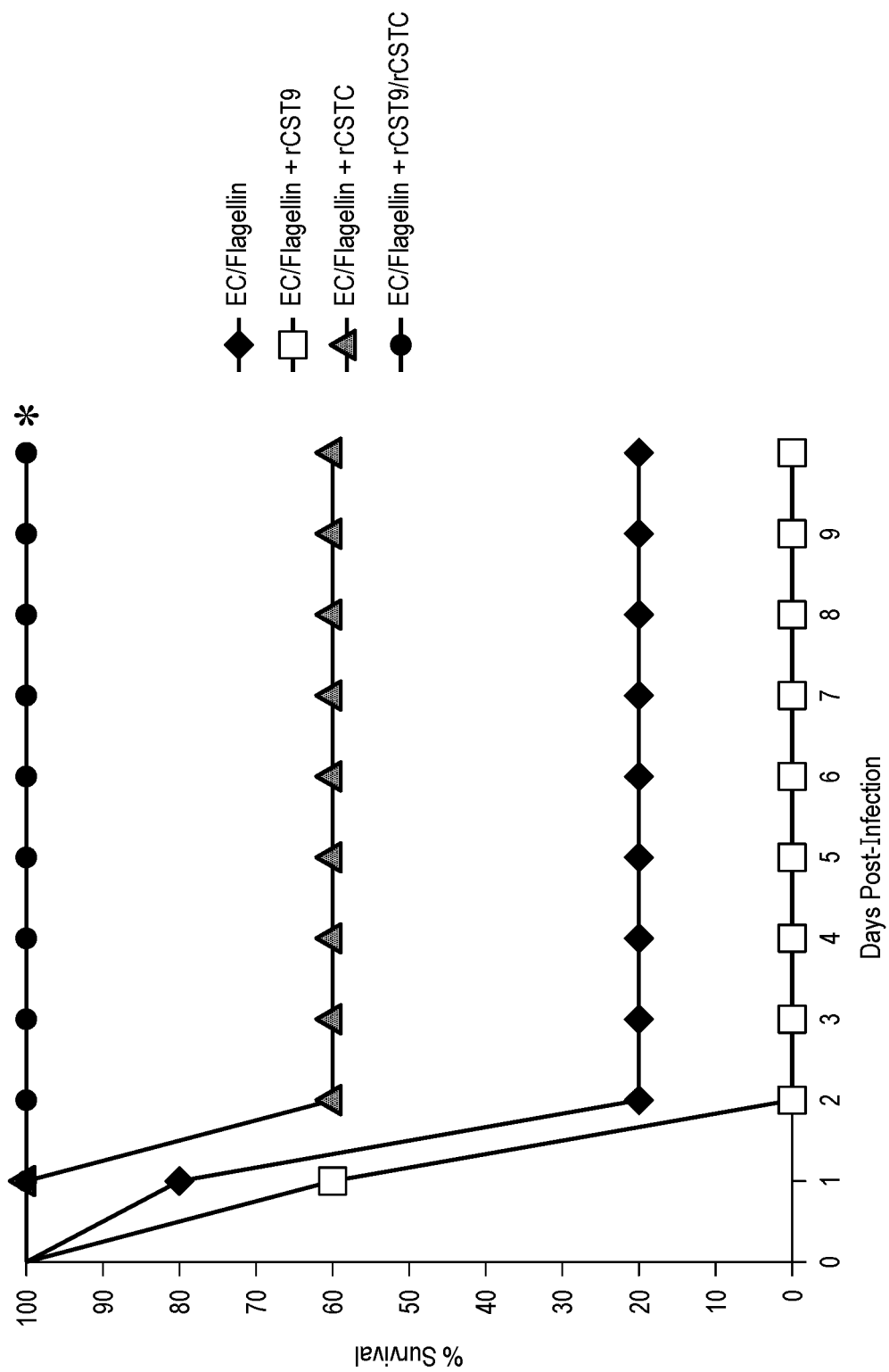
FIG. 8 shows that rCST9/rCSTC improved survival outcomes in a mouse model of infection and thermal injury. Balb/c mice (n=6/group) were given an i.p. challenge with 1000 ng of flagellin and $1\times10^7$ CFU/mouse with EC 083:H1 and treated with 500 pg of rCST9 and/or 50 pg of rCSTC then given a 30% TBSA burn injury. The individual treatment with rCST9 did not improve survival compared to rCSTC, which significantly improved survival (60%) compared to challenged and burned mice (20%; p<0.05). However, the combination treatment of rCST9/rCSTC afforded 100% survival (p<0.05). Asterisk signifies significant differences of p<0.05.
Figure 9A:
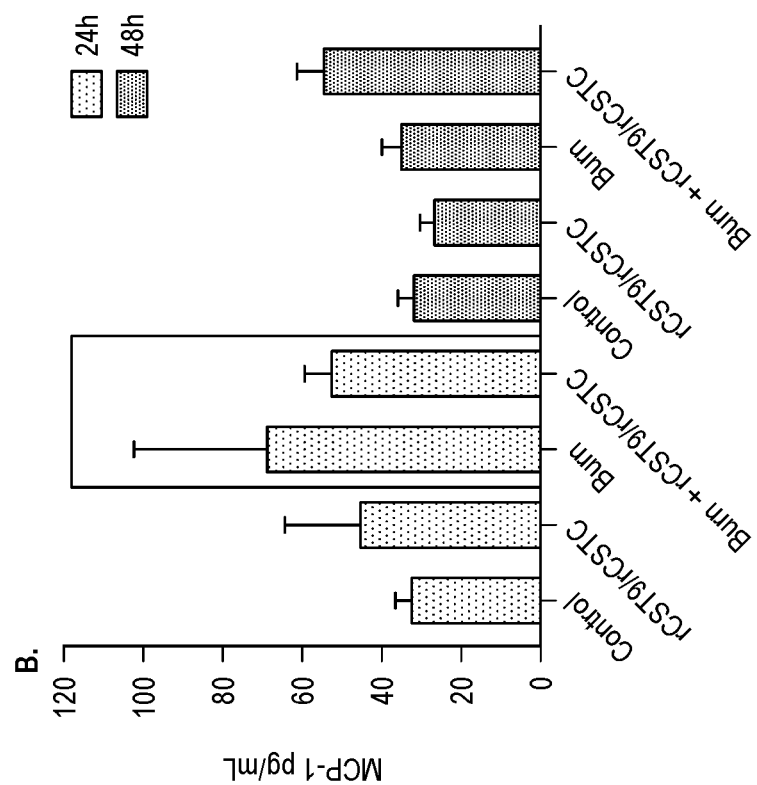
FIGS. 9A to 9E show that rCST9/rCSTC modulated cytokine secretion in a mouse model of infection and thermal injury. Balb/c mice (n=6/group) were challenged i.p. with 1000 ng of flagellin and $1\times10^7$ CFU/mouse with EC 083:H1 and treated with 500 pg of rCST9 and/or 50 pg of rCSTC then given a 30% TBSA burn injury. Serum was collected at 24 and 48 h post-burn and inflammatory cytokines quantified via a bead cytokine array. rCST9/rCSTC treatment decreased FIG. 9A) GRO-α/KC/CINC1, FIG. 9B) MCP-1, FIG. 9C) MCP-3, FIG. 9D) IP-10, and FIG. 9E) IL-6 at 24 h post-burn compared to infection and burn alone. Data are presented as mean±SEM.
Figure 9B:
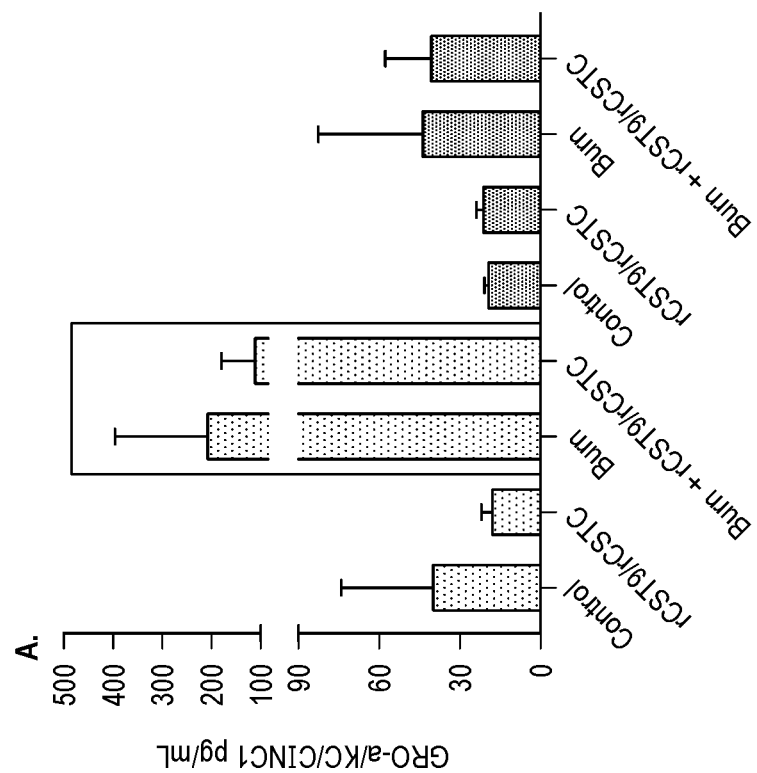
Figure 9D:
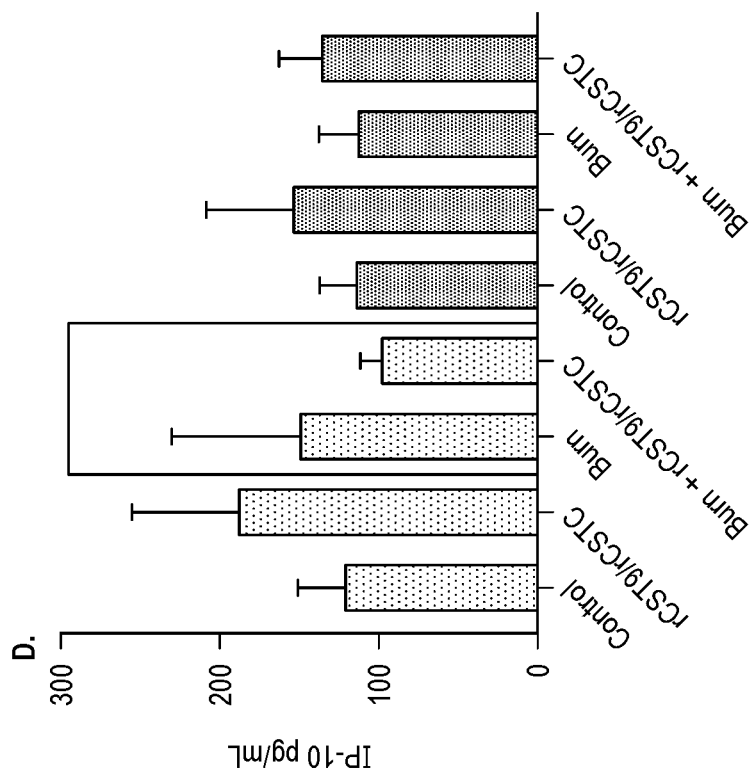
Figure 9C:
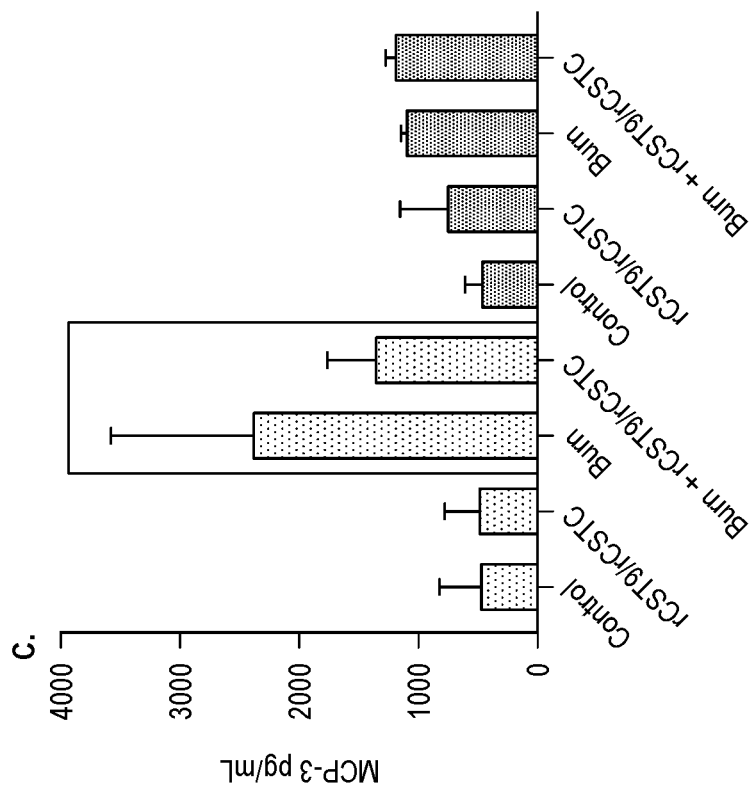
Figure 9E:
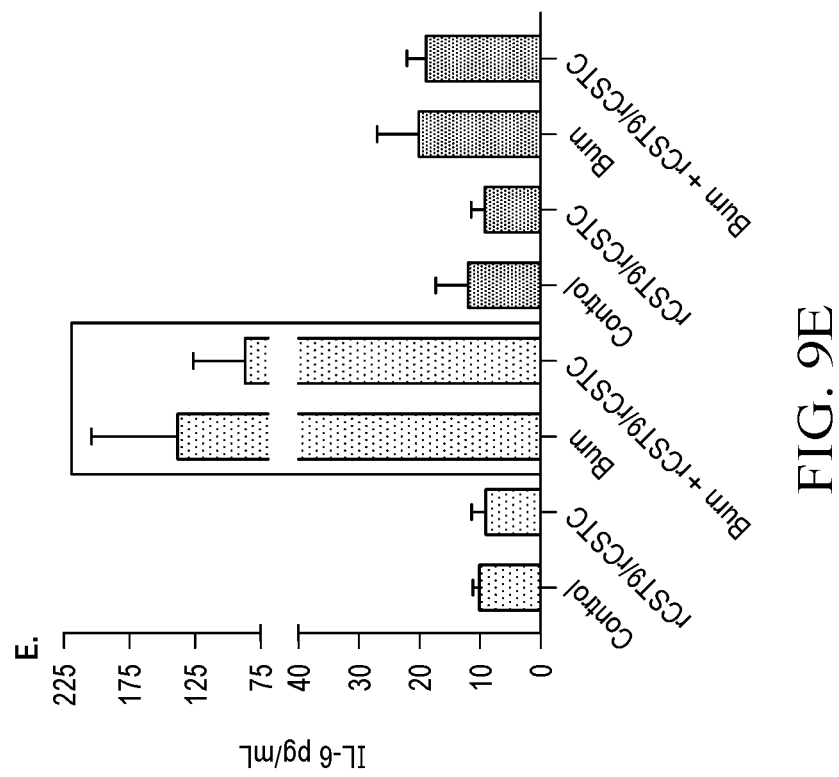

Duplicate or triplicate samples of each experimental condition were expressed as mean±SEM of two or three independent studies. Numerical data was analyzed by one-way ANOVA and Student's t-test (Prism software v7.0c, GraphPad; San Diego, CA). In vivo survival outcomes of two independent experiments were determined by Log-rank analyses with Welch's corrections using Prism software.

rCST9/rCSTC improved survival outcomes and modulated systemic cytokine secretion in a murine model of burn injury with systemic EC 083:H1 and flagellin stimulation. As shown in Example 1, rCSTs restrained damaging inflammation caused by deadly human pathogens. The synergistic combination of rCST9/rCSTC improved survival outcomes in an experimental model of thermal injury and sepsis. Balb/c mice (n=6 mice/group) were given an i.p. combination challenge of flagellin (1000 ng/mouse) and $1\times10^7$ of an intestinal organism, EC 083:H1, to represent the loss of intestinal integrity during burn injury, and then administered an i.p. injection with rCST9 (500 pg/mouse), rCSTC (50 pg/mouse), or a combination of both rCST9/rCSTC followed by a 30% TBSA burn injury. Burned mice alone served as controls. EC/flagellin challenged and burned mice treated with rCST9 alone did not improve survival (FIG. 8) while rCSTC treatment alone of EC/flagellin challenged mice significantly improved survival compared to EC/flagellin challenged mice alone and EC/flagellin rCST9-treated mice (FIG. 8; p<0.05). Similarly, the co-administration of rCST9/rCSTC to EC/flagellin challenged mice provided 100% protection following burn injury compared to EC/flagellin challenged mice alone or given rCST9 or rCSTC given as individual treatments (FIG. 8; p<0.05).

Additionally, sera was collected at 24 and 48 h post-burn from parallel groups of mice challenged with EC/flagellin, treated with the combination of rCST9/rCTC and burned as described above. These findings show that mice given an i.p. injection of rCST9/rCSTC alone did not affect cytokine secretion above baseline as compared to sham (un-challenged and un-burned) controls at either time point (FIGS. 9A-9E). At 24 h post-treatment and/or burn, sera GRO-alpha/KC/CINC1, MCP-1, MCP-3, IP-10, and IL-6, levels were down regulated in EC/flagellin challenged and burned mice treated with rCST9/rCSTC compared to burn injury alone (FIGS. 9A-9E). All tested cytokines in the sera returned to baseline by 48 h post-treatment and/or burn (FIGS. 9A-9E).

Figure 10:
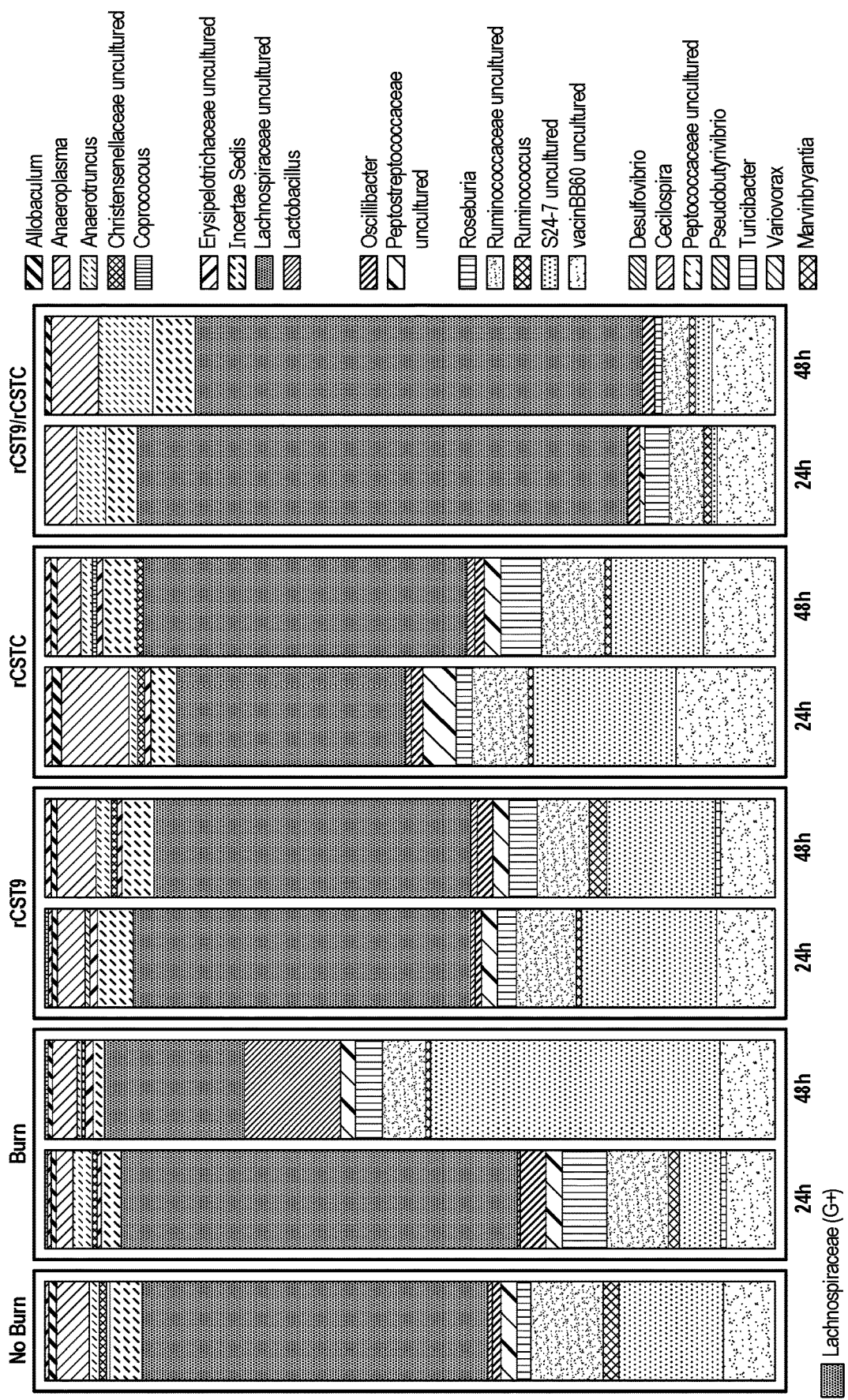
FIG. 10 shows that rCST9/rCSTC treatment preserves the gut microbiome following infection and burn injury. Balb/c mice (n=6/group) were challenged i.p. with 1000 ng of flagellin and $1\times10^7$ CFU/mouse with EC 083:H1 and treated with 500 pg of rCST9 and/or 50 pg of rCSTC then given a 30% TBSA burn injury. Intestinal samples were collected at 24 and 48 h post-burn and analyzed for microbiome profiles by 16S next generation sequencing. Infected and burned mice induced a decrease of Gram-positive *Lachnospiraceae* spp. and increase in Gram-negative S24-7. Mice treated with individual rCST9 or rCSTC preserved the gut microbiome that was equivalent to sham controls. However, rCST9/ rCSTC treatment induced the abundant growth *Lachnospiraceae* spp. with minimal detection of S24-7.

The culmination of these data showed that the co-administration of both rCSTs function as a synergistic immunotherapy to restrain, but not totally inhibit, cytokine secretion that subsequently afforded complete protection against gut-derived EC/flagellin following burn injury.

rCST9/rCSTC stabilized the gut microbiome in a murine model of burn injury with systemic EC 083:H1 and flagellin stimulation. A number of publications (1-3, 10, 11, 13), including those of the present inventors (8), have shown that burn trauma causes adverse changes in the gut microbiota, which can correlate with immune dysfunction worsening burn complications (20-22). As shown in Example 1, rCST9/rCSTC has multi-faceted functions that modulate dysregulated, damaging inflammation to promote beneficial immune responses. Therefore, the inventors determined whether rCST9/rCSTC preserves the gut microbiome following burn trauma. As such, gut samples were collected from thermally injured Balb/c mice that were i.p. challenged with EC/flagellin and/or treated with the individual rCSTs or a combination of rCST9/rCSTC at 24 or 48 h post-burn. Previously obtained normal and burn alone gut samples were used. Using next generation sequencing, accounting for sequence from greater than 90% of the bacterial 16S genes of community members present, it was found that burn trauma alone promoted changes in the gut microbiome populations with major changes at 48 h compared to sham controls (FIG. 3). The most predominate microbiome changes following burn injury was an increase in the Gram-negative *Bacteroidales* S24-7 population while the Gram-positive *Lachnospiracease* community markedly diminished at 48 h post-burn (FIG. 10). EC/Flagellin challenged mice receiving the individual rCST9 or rCST9 treatment mostly maintained the gut microbiome with minimal decrease in *Lachnospiracease* spp. and the *Bacteroidales* S24-7 population at 24 and 48 h post-burn that was comparable to sham control animals (FIG. 10). It is noteworthy to point out that at 24 h post-burn in rCSTC treated mice that there was a noticeable but moderate increase in *Bacteroidales* S24-7 with a proportionate decrease in the *Lachnospiraceae* family whereby the gut microbiome was nearly equivalent to sham controls by 48 h post-burn (FIG. 10). Conversely, EC/Flagellin challenged mice that were treated with a co-administration of rCST9/rCSTC had a marked increase in *Lachnospiraceae* spp. with a dramatic decrease in the *Bacteroidales* S24-7 family members that was scarcely detectable at 24 and 48 h post-burn (FIG. 10). These data reveal that rCST9/rCSTC poly-treatment induced changes in the gut microbiome that correlates with decreased gut-derived systemic inflammation and increased survival outcomes.

Gut-derived sepsis can occur when the integrity of the intestinal barrier is compromised following thermal injury. Leakage of intestinal bacteria and their products can move into the systemic circulation causing dysregulated, damaging inflammation resulting in morbidity and mortality (2, 3, 5, 8-10). Current treatments for burn-induced sepsis typically fail to restrain the extent and intensity of the inflammatory cascade leading to an increased risk of multiple organ failure and death (2, 3, 8). In this example, the inventors show that the immunomodulatory functions of human rCST9 and rCSTC are an innovative treatment that preserves the gut microbiome and modulates excessive inflammation leading to controlled, beneficial immune responses following thermal injury.

This example evaluated the use of a novel rCST9/rCSTC immunotherapy treatment to preserve the gut microbiome and combat dysregulated inflammation caused by gut-derived EC and flagellin following thermal injury.

Gut integrity and barrier function is compromised following thermal injury primarily due to diminished blood flow to the organ allowing disproportionate contact between enteric bacteria, their products, namely flagellin (designated flagellemia (8), and IECs igniting intestinal inflammation (2, 8, 10, 23, 24). To determine the efficacy of rCST9/rCSTC treatment against flagellemia and commensal bacteria, an established burn injury mouse model was used to examine survival outcomes, cytokine modulation and gut microbiota stability. It is shown herein that the co-administration of rCST9/rCSTC to flagellin and EC challenged mice following thermal injury afforded 100% protection compared to treatment with the individual rCSTs and burn alone. The survival outcomes in mice treated with both rCST9/rCSTC correlated with a decrease in cytokine secretion at 24 h post-burn in the sera. Hyper-production of inflammatory cytokines is a distinctive hallmark in burn patients. It has been reported that thermal injuries of 30% or greater cause excessive production of cytokines such as IL-8, MCP-1, MCP-3, MIP-1β and IL-6 (26, 27) which can be a measure of patient outcomes. Following thermal injury, circulating IL-6 has been found to be elevated in both mouse and human sera (28, 29). IL-6 plays a crucial role mediating hypermetabolic stress responses in burn patients that contributes to sepsis, multiple organ failure (MOF) as well as morbidity and mortality (30-32). rCST9/rCSTC treatment specifically decreased the cytokine IL-6 as well as various chemokines such as MCP-1, GRO-α/KC(IL-8)/CINC1, IP-10 and MCP-3. It has been vastly reported that elevated and prolonged secretion of inflammatory chemokines can cause the excessive infiltration of immune cells into tissues leading to further exasperation of inflammation and subsequent organ damage and MOF (31, 32). Therefore, the restraint, but not complete inhibition, of these cytokines, as a result of rCST9/rCSTC treatment allows for manageable, beneficial host immune responses to effectively combat gut-derived systemic inflammation caused by thermal injury trauma ultimately improving survival outcomes.

The effects of rCST9/rCSTC on the gut microbiome in mice given an i.p. challenge of flagellin and EC to represent the escape of bacteria and their products from the intestine following by a 30% TBSA burn injury was evaluated. Intestinal samples were collected from the same mice from which sera was collected for cytokine analysis. Although the total number of bacterial species in the gut microbiome did not change significantly between the tested experimental groups, the shift in two bacterial species was markedly affected post-burn and treatment. Specifically, flagellin/EC challenged and burned mice showed a substantial increase in Gram-negative group of the *Bacteroidales* known as S24-7 and decrease in Gram-positive *Lachnospiraceae* spp at 48 h post-burn compared to sham controls. Interestingly, the individual treatment of rCST9 or rCSTC maintained a gut microbiome profile that was nearly equivalent to sham control mice with *Lachnospiraceae* spp being the predominate microbiota detected in the gut while the population of S24-7 was minimal. The gut microbiome communities remained essentially unchanged over time in mice either receiving an individual rCST treatment. The combination treatment of rCST9/rCSTC was overwhelmingly *Lachnospiraceae* spp with negligible detection of S24-7. *Lachospiraceae* spp produce short chain fatty acids that are known to confer a variety of health benefits such as energy sources for colonic cells and increased mucin production (34) and are associated with maintaining intestinal barrier functions (35).

Thus, a single, small dose of rCST9/rCSTC worked in a synergistic and multi-faceted manner to modulate pathogenic systemic inflammation and preserve a 'healthy' gut microbiome. Maintaining and stabilizing the gut microbiome, as shown with the rCST9/rCSTC treatment, restrains pathogenic systemic inflammation and multiple organ dysfunction syndrome (MODS) induced by burn injury and other traumas. Finally, the co-administration of rCST9/rCSTC may be used alone, or in combination with less toxic or otherwise suboptimal antibiotic dosages, to combat gut-derived sepsis and dysregulated inflammation ultimately improving patient outcomes.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

References—Example 1

1. Loffek S, Schilling O, Franzke C W. 2011. Series Matrix metalloproteinases in lung health and disease: Biological role of matrix metalloproteinases: a critical balance. Eur Respir J 38:191-208.
2. Zavasnik-Bergant T. 2008. Cystatin protease inhibitors and immune functions. Front Biosci 13:4625-4637.
3. Ochieng J, Chaudhuri G. 2010. Cystatin superfamily. J Health Care Poor Underserved 21:51-70.
4. Bobek L A, Levine M J. 1992. Cystatins—inhibitors of cysteine proteinases. Crit Rev Oral Biol Med 3:307-332.
5. Kopitar-Jerala N. 2006. The role of cystatins in cells of the immune system. FEBS Lett 580:6295-6301.
6. Poteryaeva O N, Falameyeva O V, Korolenko T A, Kaledin V I, Djanayeva S J, Nowicky J W, Sandula J. 2000. Cysteine proteinase inhibitor level in tumor and normal tissues in control and cured mice. Drugs Exp Clin Res 26:301-306.
7. Vray B, Hartmann S, Hoebeke J. 2002. Immunomodulatory properties of cystatins. Cell Mol Life Sci 59:1503-1512.
8. Gauthier S, Kaur G, Mi W, Tizon B, Levy E. 2011. Protective mechanisms by cystatin C in neurodegenerative diseases. Front Biosci (Schol Ed) 3:541-554.
9. Kaeser S, Herzig M, Coomaraswamy J, Kilger E, Selenica M, Winkler D, Staufenbiel M, Levy E, Grubb A, Jucker M. 2007. Cystatin C modulates cerebral-amyloidosis. Nat Genet 39, 1437-1439
10. Kaur G, Levy E. 2012. Cystatin C in Alzheimer's disease. Front Mol Neurosci 5:79.
11. Ervin H, Cox J L. 2005. Late stage inhibition of hematogenous melanoma metastasis by cystatin C overexpression. Cancer Cell Int 5:14.

12. Tian M, Schiemann W P. 2009. Preclinical Efficacy of Cystatin C to Target the Oncogenic Activity of Transforming Growth Factor β in Breast Cancer. Transl Oncol 2:174-183.
13. Magister Š, Kos J. 2013. Cystatins in Immune System. J Cancer 4:45-56.
14. Rivera L E, Colón K, Cantres-Rosario Y M, Zenón F M, Meléndez L M. 2014. Macrophage derived cystatin B/cathepsin B in HIV replication and neuropathogenesis. Curr HIV Res 12:111-120.
15. Eaves-Pyles T, Patel J, Arigi E, Cong Y, Cao A, Garg N, Dhiman M, Pyles R B, Arulanandam B, Miller A L, Popov V L, Soong L, Carlsen E D, Coletta C, Szabo C, Almeida I C. 2013. Immunomodulatory and antibacterial effects of cystatin 9 against *Francisella tularensis*. Mol Med 19: 263-275.
16. Khalil M A F, Elgaml A, El-Mowafy M. 2017. Emergence of Multidrug-Resistant New Delhi Metallo-β-Lactamase-1-Producing *Klebsiella pneumoniae* in Egypt. Microb Drug Resist 23:480-487.
17. Khan A U, Maryam L, Zarrilli R. 2017. Structure, Genetics and Worldwide Spread of New Delhi Metallo-β-lactamase (NDM): a threat to public health. BMC Microbiol 17:101.
18. Halaby T, Reuland A E, Naiemi N, Potron A, Savelkoul P H, Vanenbrouke-Grauls C M, Nordmann P. 2012. A Case of New Delhi Metallo-β-Lactamase 1 (NDM-1)-Producing *Klebsiella pneumoniae* with Putative Secondary Transmission from the Balkan Region in the Netherlands. Antimicrob Agents Chemother 56:2790-2791.
19. Pesesky M W, Hussain T, Wallace M, Wang B, Andleeb S, Burnham C D, Dantas G. 2015. KPC and NDM-1 Genes in Related Enterobacteriaceae Strains and Plasmids from Pakistan and the United States. J Emerg Infect Dis 21:1034-1037.
20. Barantsevich E P, Churkina I V, Barantsevich N E, Pelkonen J, Schlyakhto E V, Woodford N. 2013. Emergence of *Klebsiella pneumoniae* producing NDM-1 carbapenemase in Saint Petersburg, Russia, J Antimicrob Chemother 68:1204-6
21. Bosch T, Lutgens S P M, Hermans M H A, Wever P C, Schneeberger P M, Renders N H M, Leenders ACAP, Kluytmans JAJW, Schoffelen A, Notermans D, Witteveen S, Bathoorn E, Schouls L M. 2017. Outbreak of NDM-1-Producing *Klebsiella pneumoniae* in a Dutch Hospital, with Interspecies Transfer of the Resistance Plasmid and Unexpected Occurrence in Unrelated Health Care Centers. J Clin Microbiol 55:2380-2390.
22. Li J J, Munoz-Price L S, Spychala C N, DePascale D, Doi Y. 2016. New Delhi Metallo-β-Lactamase-1-Producing *Klebsiella pneumoniae*, Florida, USA. Emerg Infect Dis 22:744-6.
23. Lee C-R, Lee J H, Park K S, Kim Y B, Jeong B C, Lee S H. 2016. Global Dissemination of Carbapenemase-Producing *Klebsiella pneumoniae*: Epidemiology, Genetic Context, Treatment Options, and Detection Methods. Front Microbiol 7:895.
24. Pitout J D, Nordmann P, Poirel L. 2015. Carbapenemase-Producing *Klebsiella pneumoniae*, a Key Pathogen Set for Global Nosocomial Dominance. Antimicrob Agents Chemother 59:5873-84.
25. Hudson C M, Bent Z W, Meagher R J, Williams K P. 2014. Resistance Determinants and Mobile Genetic Elements of an NDM-1-Encoding *Klebsiella pneumoniae* Strain. PLoS ONE 9: e99209.
26. Robilotti E and Deresinski S. 2014. Carbapenemase-producing *Klebsiella pneumoniae*. F1000Prime Rep 6: 80.
27. Liang Z, Li L, Wang Y, Chen L, Kong X, Hong Y, Lan L, Zheng M, Guang-Yang C, Liu H, Shen X, Lou C, Li K, Chen K, Jiang H. 2011. Molecular Basis of NDM-1, a New Antibiotic Resistance Determinant. PLOS ONE 6: e23606.
28. Zmarlicka M T, Nailor M D, Nicolau D P. 2015. Impact of the New Delhi metallo-beta-lactamase on beta-lactam antibiotics. Infect Drug Resist 8:297-309.
29. Zhu K, Lu J, Liang Z, Kong X, Ye F, Jin L, Geng H, Chen Y, Zheng M, Jiang H, Li J Q, Luo C. 2013. A quantum mechanics/molecular mechanics study on the hydrolysis mechanism of New Delhi metallo-β-lactamase-1. J Comput Aided Mol Des 27:247-56
30. Bauer T T, Ewig S, Rodloff A C, and Muller E. 2006. Acute respiratory distress syndrome and pneumonia: a comprehensive review of clinical data. Clin Infect Dis 43:748-756.
31. Okamoto T, Akuta T, Tamura F, van Der Vliet A, Akaike T. 2004. Molecular mechanism for activation and regulation of matrix metalloproteinases during bacterial infections and respiratory inflammation. Biol Chem 385:997-1006.
32. Hickman-Davis J M, O'Reilly P, Davis I C, Peti-Peterdi, Davis G, Young R, Devlin R B, and Matalon S. 2002. Killing of *Klebsiella pneumonia* by human alveolar macrophages. Am J Physiol Lung Cell Mol Physiol 282: L944-L956.33.
33. Docobo-Pérez F, Nordmann P, Domínguez-Herrera J, López-Rojas R, Smani Y, Poirel L, Pachón J. 2011. Efficacies of colistin and tigecycline in mice with experimental pneumonia due to NDM-1-producing strains of *Klebsiella pneumoniae* and *Escherichia coli*. Int J Antimicrob Agents 39:251-4.
34. Mattheolabakis G, Wong C C, Sun Y, Amella C A, Richards R, Constantinides P P, Rigas B. 2014. Pegylation improves the pharmacokinetics and bioavailability of small-molecule drugs hydrolyzable by esterases: a study of phospho-Ibuprofen. J Pharmacol Exp Ther 351:61-635.
35. Harris J M, Chess R B. 2003. Effect of pegylation on pharmaceuticals. Nat Rev Drug Discov 2:214-21.
36. Gurjar M. 2015. Colistin for lung infection: an update. J Intensive Care 3:3.
37. Falagas M E, Kasiakou S K. 2005. Colistin: the revival of polymyxins for the management of multidrug-resistant gram-negative bacterial infections. Clin Infect Dis 40:1333-41.
38. Cimerman N, Kosorok M D, Korant B D, Turk B, Turk V. 1996. Characterization of cystatin C from bovine parotid glands: cysteine proteinase inhibition and antiviral properties. Biol Chem Hoppe Seyler 377:19-23.
39. Björck L, Grubb A, Kjellén L. 1990. Cystatin C, a human proteinase inhibitor, blocks replication of herpes simplex virus. J Virol 64:941-3.
40. Kar S, Ukil A, Das P K. 2011. Cystatin cures visceral leishmaniasis by NF-κB-mediated proinflammatory response through co-ordination of TLR/MyD88 signaling with p105-Tp12-ERK pathway. Eur J Immunol 41:116-27.
41. Eaves-Pyles T D, Wong H R, Odoms K, Pyles R B. 2001. *Salmonella* flagellin-dependent proinflammatory responses are localized to the conserved amino and carboxyl regions of the protein. J Immunol 167:7009-16.

42. Pyles R B, Jezek G E, Eaves-Pyles T D. 2010. Toll-Like Receptor 3 Agonist Protection against Experimental *Francisella tularensis* Respiratory Tract Infection. Infect Immun 78:1700-1710.
43. Coban A Y. 2012. Rapid determination of methicillin resistance among Staphyloccus *aureus* clinical isolates by colorimetric methods. J Clin Micro 50: 2191-2193.

References—Example 2

1. Martin R, Miguel S, Ulmer J, Kechaou N, Langella P, Bermúdez-Humarán L G. Role of commensal and probiotic bacteria in human health: a focus on inflammatory bowel disease. Microb Cell Fact. 2013; 12:71.
2. Magnotti L J, Deitch E A. Burns, bacterial translocation, gut barrier function, and failure. J Burn Rehabil. 2005; 26:383.
3. Youn Y K, LaLonde C, Demling R. The role of mediators in the response to thermal injury. World J Surg. 1992; 16:30.
4. Li N, Quidgley M C, Kobeissy F H, Joseph J, Neu J. Microbial cell components induced tolerance to flagellin-stimulated inflammation through Toll-like receptor pathways in intestinal epithelial cells. Cytokine. 2012; 60:806.
5. Qin L, Wu X, Block M L, Liu Y, Breese G R, Hong J S, Knapp D J Crews F T. Systemic LPS causes chronic neuroinflammation and progressive neurodegeneration. Glia. 2007; 55:453.
6. Yoon S I, Kurnasov O, Natarajan V, Hong M, Gudkov A V, Osterman A L, Wilson I A. Structural basis of TLR5-flagellin recognition and signaling. Science. 2012; 335:859.
7. Carvalho F A, Aitken J D, Gewirtz A T, Vijay-Kumar M. TLR5 activation induces secretory interleukin-1 receptor antagonist (sIL-1Ra) and reduces inflammasome-associated tissue damage. Mucosal Immunol. 2010; 4:102.
8. Grimes L, Doyle A, Miller A L, Pyles R B, Olah G, Szabo C, Hoskinson S, Eaves-Pyles, T. Intraluminal Flagellin Differentially Contributes to Gut Dysbiosis and Systemic Inflammation following Burn Injury. PLoS One. 2016; 11:e0166770.
9. Greenhalgh D G. Sepsis in the burn patient: a different problem than sepsis in the general population. Burns Trauma. 2017; 5:23.
10. Earley Z M. Akhtar S, Green S J, NaqibA, Khan O, Cannon A R, Hammer A M, Morris N L, Li X, Eberhardt J M, Gamelli R L, Kennedy R H, Choudhry, M A. Burn Injury Alters the Intestinal Microbiome and Increases Gut Permeability and Bacterial Translocation. PloS one. 2015; e0129996.
11. Howard B M, Kornblith L Z, Christie S A, Conroy A S, Nelson M F, Campion E M, Callcut R A, Calfee C S, Lamere B J, Fadrosh D W, Lynch S, Cohen, M J. 2017. Characterizing the gut microbiome in trauma: significant changes in microbial diversity occur early after severe injury. Trauma Surg Acute Care Open. 2017; 2:e000108. doi:10.1136/tsaco-2017-000108.
12. Dacso C C, Luterman A, Curreri P W. Systemic antibiotic treatment in burned patients. Surg Clin North Am. 1987; 67:57.
13. Yoon M Y, Yoon S S. Disruption of the Gut Ecosystem by Antibiotics. Yonsei Med J. 201759:4-12.
14. Eaves-Pyles T, Patel J, Arigi E, Cong Y, Cao A, Garg N, Dhiman M, Pyles R B, Arulanandam B, Miller A L, Popov V L, Soong L, Carlsen E D, Coletta C, Szabo C, Almeida I C. Immunomodulatory and antibacterial effects of cystatin 9 against *Francisella tularensis*. Mol Med. 2013; 19: 263.
15. Holloway A, Yu J, Arulanandam B, Hoskinson S, Eaves-Pyles T. Cystatin 9 and C: A novel immunotherapy that protects against multi-drug resistant New Dehli metallo-beta-lactamase-1 producing *Klebsiella Pneumoniae*. Antimicrob Agents Chemother 2017; 62:e01900-17.
16. Zavasnik-Bergant T. Cystatin protease inhibitors and immune functions. Front Biosci 2008; 13:4625.
17. Ochieng J, Chaudhuri G. Cystatin superfamily. J Health Care Poor Underserved 2010; 21:51.
18. Magister S, Kos J. Cystatins in immune system. J Cancer. 2012; 4:45.
19. Parhar K, Ray A, Steinbrecher U, Nelson C, Salh B. The p38 mitogen-activated protein kinase regulates interleukin-1beta-induced IL-8 expression via an effect on the IL-8 promoter in intestinal epithelial cells. Immunology. 2003; 108:50212.
20. Fear V S, Boyd J H, Rea S, Wood F M, Duke J M, Fear M W. Burn Injury Leads to Increased Long-Term Susceptibility to Respiratory Infection in both Mouse Models and Population Studies. PLoS One. 2017; 12:e0169302.
21. Fayazov A D, Shukurov S I, Shukurov B I, Sultanov B C, Namazov A N, Ruzimuratov D A. Disorders of the immune system in severely burned patients. Ann Burns Fire Disasters. 2009; 22:121.
22. Nielson C B, Duethman N C, Howard J M, Moncure M, Wood J G. Burns: Pathophysiology of Systemic Complications and Current Management. J Burn Care Res. 2016; 38:e469-e481.
23. Huang G, Sun K, Yin S, Jiang B, Chen Y, Gong Y, Chen Y, Yang Z, Chen J, Yuan Z Peng Y. Burn Injury Leads to Increase in Relative Abundance of Opportunistic Pathogens in the Rat Gastrointestinal Microbiome. Front Microbiol. 2017; 8:1237.
24. Wang X, Yang J, Tian F, Zhang L, Lei Q, Jiang T, Zhou J, Yuan S, Wang J, Feng Z, Li J. Gut microbiota trajectory in patients with severe burn: A time series study. J Crit Care. 2017; 42:310.
25. Jonathan S P and Schiemann W P. Cystatin C antagonizes transforming growth factor b signaling in normal and cancer cells. Mole Cancer Res. 2004; 2:183-195
26. Jeschke M G, Chinkes D L, Finnerty C C, Kulp G, Suman O E, Norbury W B, Branski L K, Gauglitz G G, and Mlcak R P, Herndon D N. The pathophysiologic response of severe burn injury. Ann. Surg. 2008; 248:387.
27. Finnerty C C, Jeschke M G, DN, Gamelli R L, Gibran N S, Klein M B, Silver G M, Arnoldo B, Remick D G, Tompkins R G. Temporal cytokine profiles in severely burned patients: a comparison of adults and children. Mol Med. 2008; 14: 553.
28. Yeh F L, Lin W L, Shen H D, Fang R H. Changes in circulating levels of interleukin-6 in burned patients. Burns 1999; 2:131.
29. Abdullahi A, Chen P, Stanojcic M, Safri A R Coburn N, Jeschke M G. IL-6 signal from the bone marrow is required for the broning of white adipose tissue post burn injury. Shock. 2017; 47:33.
30. Jeschke M G, Gauglitz G Gm Kulp G A, Finnerty C Cm Williams F N, Kraft R, Suman O E, Mlcak R P, Herndon D N. Long-term persistence of the pathophysiologic response to severe burn injury. PLosOne. 2011; 6:e21245
31. Bortolin J A, Quintana H T, Tomé T C, Ribeiro F A P, Ribeiro D A, and Oliveira F D. Burn injury induces histopathological changes and cell proliferation in liver of rats. World J Hepatol. 2016; 8: 322.

32. Dunn J L M, Kartchner L B, Stepp W H, Glenn L I, Malfitano M M, Jones S W, Doerschuk C M, Maile R, Cairns B A. Blocking CXCL1-dependent neutrophil recruitment prevents immune damage and reduces pulmonary bacterial infection after inhalation injury. Am J Physiol Lung Cell Mol Physiol. 2018; 314:L822.
33. Kang C, Wang B, Kaliannan K, Wang X, Lang H, Hui S, Huang L, Zhang Y, Zhou M, Chen M, Mi M. Gut Microbiota Mediates the Protective Effects of Dietary Capsaicin against Chronic Low-Grade Inflammation and Associated Obesity Induced by High-Fat Diet. MBio. 2017; e00470-17.
34. Matsuoka K, Kanai T. The gut microbiota and inflammatory bowel disease. Semin Immunopathol. 2015; 37:47.
35. Krych Ł, Nielsen D S, Hansen A K, Hansen C H. Gut microbial markers are associated with diabetes onset, regulatory imbalance, and IFN-γ level in NOD mice. Gut Microbes. 2015; 6:101.
36. Shimizu K, Ogura H, Asahara T, Nomoto K, Matsushima A, Hayakawa K, Ikegawa H2, Tasaki O, Kuwagata Y, Shimazu T. Gut microbiota and environment in patients with major burns—a preliminary report. Burns 2015; 41:e28.

What is claimed is:

1. A method of treating or restraining a life-threatening, unrestrained systemic inflammatory response syndrome (SIRS) in a host lung cell against multidrug resistant *Klebsiella pneumoniae* by increasing the survival of a mammal comprising:

identifying the mammal in need of treatment for the SIRS; and providing the mammal with a recombinant Cystatin 9 (CST9) and Cystatin C (CSTC) in a synergistic amount sufficient to treat or restrain SIRS, wherein the synergistic amount comprises 500 pg of rCST9 per kilogram of body weight and 50 pg or 500 pg of rCSTC per kilogram of body weight, which amount can vary by up to 15%, wherein the combination of rCST9 and rCSTC are administered at the same time intraperitoneally; and wherein sepsis is treated or restrained as the life-threatening, unrestrained SIRS thereby increasing survival of the mammal; wherein the recombinant CST9 and CSTC are provided 1, 2, or 3 days post infection.

2. The method of claim 1, wherein the rCST9/rCSTC reduces systemic monocyte chemoattractant protein-1 (MCP-1), monocyte chemoattractant protein-3 (MCP-3), interferon gamma-induced protein (IP-10), interleukin-6 (IL-6), and growth-related oncogene alpha/equivalent to human interleukin-8/cytokine-induced neutrophil chemoattractant (GRO-alpha/KC) at 24 h post-infection.

3. The method of claim 1, wherein the rCST9 and rCSTC are formulated for intraperitoneal, intravenous, parenteral, enteral, pulmonary, intranasal, intramuscular, rectal, or oral administration.

4. The method of claim 1, wherein the recombinant Cystatin 9 (CST9) is 500 picograms/kilogram of body weight of the mammal and Cystatin C (CSTC) is 50 picograms/kilograms body weight of the mammal.

5. The method of claim 1, wherein the recombinant Cystatin 9 (CST9) and Cystatin C (CSTC) are PEGylated.

6. The method of claim 1, wherein the mammal is a human.

* * * * *